US009005130B2

United States Patent
Fischell et al.

(10) Patent No.: US 9,005,130 B2
(45) Date of Patent: Apr. 14, 2015

(54) HISTOGRAM BASED GENERATION OF CARDIAC STATE DETECTION THRESHOLDS

(71) Applicant: Angel Medical Systems, Inc., Fair Haven, NJ (US)

(72) Inventors: David R. Fischell, Fair Haven, NJ (US); Robert E. Fischell, Dayton, MD (US); Jonathan Harwood, Rumson, NJ (US); Steven R. Johnson, Fair Haven, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

(21) Appl. No.: 14/101,499

(22) Filed: Dec. 10, 2013

(65) Prior Publication Data

US 2014/0107514 A1 Apr. 17, 2014

Related U.S. Application Data

(63) Continuation of application No. 13/461,100, filed on May 1, 2012, now Pat. No. 8,655,434, and a continuation of application No. 12/320,948, filed on Feb. 10, 2009, now Pat. No. 8,244,338, and a continuation of application No. 10/950,401, filed on Sep. 28, 2004, now Pat. No. 7,512,438.

(60) Provisional application No. 60/524,873, filed on Nov. 26, 2003.

(51) Int. Cl.
| | |
|---|---|
| *A61B 5/0452* | (2006.01) |
| *A61B 5/0472* | (2006.01) |
| *A61B 5/00* | (2006.01) |
| *A61N 1/02* | (2006.01) |

(Continued)

(52) U.S. Cl.
CPC .............. *A61B 5/0472* (2013.01); *A61B 5/0031* (2013.01); *A61B 5/0452* (2013.01); *A61B 5/413* (2013.01); *A61N 1/025* (2013.01); *A61N 1/37211* (2013.01); *A61N 1/37247* (2013.01); *A61B 5/0006* (2013.01); *A61B 5/02405* (2013.01); *A61B 5/02455* (2013.01); *A61B 5/04012* (2013.01); *A61B 5/042* (2013.01); *A61B 5/0432* (2013.01); *A61B 5/044* (2013.01); *A61B 5/686* (2013.01); *A61B 5/746* (2013.01)

(58) Field of Classification Search
USPC ........................................ 600/508, 516, 518
See application file for complete search history.

(56) References Cited

U.S. PATENT DOCUMENTS

| 4,336,810 A | 6/1982 | Anderson et al. |
| 4,513,743 A | 4/1985 | van Arragon et al. |

(Continued)

OTHER PUBLICATIONS

Warnecke, H., et al., "Clinical Heart Transplantation without Routine Endomyocardial Biopsy", The Journal of Heart and Lung Transplantation, vol. 11, No. 6, Nov./Dec. 1992, pp. 1093-1102.

(Continued)

*Primary Examiner* — Christopher D Koharski
*Assistant Examiner* — Natasha Patel
(74) *Attorney, Agent, or Firm* — Rosenberg, Klein & Lee

(57) ABSTRACT

A method for tracking cardiac conditions is disclosed. An electrical signal from a patient's heart is sensed. A heart signal parameter value and an associated heart rate value are computed from the electrical signal. Based on the heart rate value, one of a plurality of histograms stored in a histogram memory is updated with the heart signal parameter value. After a data collection time period has elapsed, a statistical value of the heart signal parameter is computed from the selected histogram. A detection threshold for abnormal values of the heart signal parameter is then computed based on the statistical value.

9 Claims, 11 Drawing Sheets

(51) Int. Cl.

| | | |
|---|---|---|
| *A61N 1/372* | (2006.01) | |
| *A61B 5/024* | (2006.01) | |
| *A61B 5/0245* | (2006.01) | |
| *A61B 5/04* | (2006.01) | |
| *A61B 5/042* | (2006.01) | |
| *A61B 5/0432* | (2006.01) | |
| *A61B 5/044* | (2006.01) | |

(56) References Cited

U.S. PATENT DOCUMENTS

| | | |
|---|---|---|
| 4,905,707 A | 3/1990 | Davies et al. |
| 5,042,497 A | 8/1991 | Shapland |
| 5,088,488 A | 2/1992 | Markowitz et al. |
| 5,113,869 A | 5/1992 | Nappholz et al. |
| 5,135,004 A | 8/1992 | Adams et al. |
| 5,139,028 A | 8/1992 | Steinhaus et al. |
| 5,313,953 A | 5/1994 | Yomtov et al. |
| 5,402,794 A | 4/1995 | Wahlstrand et al. |
| 5,411,031 A | 5/1995 | Yomtov |
| 5,497,780 A | 3/1996 | Zehender |
| 5,792,047 A | 8/1998 | Coggins |
| 5,891,048 A | 4/1999 | Nigam et al. |
| 6,112,116 A | 8/2000 | Fischell et al. |
| 6,128,526 A | 10/2000 | Stadler et al. |
| 6,230,049 B1 | 5/2001 | Fischell et al. |
| 6,272,379 B1 | 8/2001 | Fischell et al. |
| 6,368,284 B1 | 4/2002 | Bardy |
| 6,501,983 B1 | 12/2002 | Natarajan et al. |
| 6,572,557 B2 | 6/2003 | Tchou et al. |
| 6,609,023 B1 | 8/2003 | Fischell et al. |
| 6,714,811 B1 | 3/2004 | Padmanabhan et al. |
| 6,847,905 B2 | 1/2005 | Etheridge et al. |
| 7,043,301 B1 | 5/2006 | Kroll et al. |
| 7,766,826 B2 * | 8/2010 | Lee et al. .................. 600/300 |
| 2002/0095095 A1 | 7/2002 | Callahan et al. |
| 2006/0064136 A1 | 3/2006 | Wang |

OTHER PUBLICATIONS

Knosalla, C., et al., "Intramyocardial Electrogram Recordings (IMEG) for Diagnosis of Cellular and Humoral Mediated Cardiac Allograft Rejection", Annals of Thoracic and Cardiovascular Surgery (ATCS), vol. 6, No. 2, 2000, pp. 89-94.

* cited by examiner

HISTOGRAM BASED GENERATION OF CARDIAC STATE DETECTION THRESHOLDS

CROSS REFERENCE TO RELATED APPLICATIONS

This application is a Continuation of patent application Ser. No. 13/461,100, filed 1 May 2012, currently pending, which is a Continuation of patent application Ser. No. 12/320,948 filed on 10 Feb. 2009, now U.S. Pat. No. 8,244,338, issued 14 Aug. 2012 which is a continuation-in-part of Ser. No. 10/950, 401 filed on 28 Sep. 2004, now U.S. Pat. No. 7,512,438, issued 31 Mar. 2009, which was based upon Provisional Patent Application No. 60/524,873, filed on 26 Nov. 2003.

FIELD OF USE

This invention is in the field of systems that monitor a patient's cardiovascular condition using implanted devices that interact with other devices located externally to the patient.

BACKGROUND OF THE INVENTION

Heart disease is the leading cause of death in the United States. A heart attack (also known as an acute myocardial infarction (AMI)) typically results from a thrombus (i.e., a blood clot) that obstructs blood flow in one or more coronary arteries. AMI is a common and life-threatening complication of coronary artery disease. Myocardial ischemia is caused by an insufficiency of oxygen to the heart muscle. Ischemia is typically provoked by physical activity or other causes of increased heart rate when at least one coronary artery is narrowed by atherosclerosis. Patients will often (but not always) experience chest discomfort (angina) when the heart muscle is experiencing ischemia. Those with coronary atherosclerosis are at higher risk for AMI if the plaque becomes further obstructed by thrombus. Those patients who do not have any symptom of ischemia or AMI are said to have "silent ischemia." These patients are at the highest risk of dying from coronary artery disease.

The current treatment for a coronary artery narrowing (a stenosis) is the insertion of a drug eluting stent such as the Cypher™ sirolimus-eluting stent from Cordis Corporation or the Taxus™ paclitaxel-eluting stent from the Boston Scientific Corporation. The insertion of a stent into a stenosed coronary artery is the most reliable medical treatment to eliminate or reduce coronary ischemia and to prevent the complete blockage of a coronary artery, which complete blockage results in an AMI.

Acute myocardial infarction and ischemia may be detected from a patient's electrocardiogram (ECG) by noting an ST segment shift (i.e., voltage change) over a relatively short (less than 5 minutes) period of time after a complete blockage of a coronary artery. However, without knowing the patient's normal (i.e., baseline) ECG pattern, detection from a standard 12 lead ECG can be unreliable.

Fischell, et al in U.S. Pat. Nos. 6,112,116, 6,272,379 and 6,609,023 describe implantable systems and algorithms for detecting the onset of acute myocardial infarction and providing both treatment and patient alerting. While Fischell, et al discuss the acute detection of a shift in the ST segment of the patient's electrogram from an electrode within the heart as the trigger for alarms, it may be desirable to provide more sophisticated long term tracking of myocardial ischemia to provide early prediction of coronary obstruction before the occurrence of a complete coronary artery blockage that results in an AMI. An important aspect of the Fischell, et al patents is that the heart's electrical signal from inside the patient's body, which is called an "electrogram," is a more accurate means to discern ischemia as compared to the heart's signal as measured on the patient's skin which is the ECG.

The Fischell, et al patents as listed above discuss the storage of recorded electrograms and/or electrocardiogram data; however techniques to optimally capture the appropriate statistical electrogram and/or electrocardiogram data over days, weeks and months in a limited amount of system memory are not described.

The Reveal™ subcutaneous loop Holter monitor sold by Medtronic, Inc. uses two case electrodes spaced about 3 inches apart to record electrogram information. Recording can be triggered automatically when arrhythmias are detected or upon patient initiation using an external device. The Reveal is designed to record electrogram data and does not include the signal processing capability to track changes in the heart signal over an extended period of time. The Reveal also does not have the capability to measure ST segment shift. In fact, its high pass filtering and electrode spacing preclude accurate detection of changes in the low frequency aspects of the heart's electrical signal, which low frequency aspects are required for the detection of ischemia.

While pacemakers track the numbers of beats paced or not paced and pacemaker programmers can display the beat data in histogram format, pacemakers do not produce histograms of heart signal parameters related to the electrogram wave form. In other words, pacemakers track pacemaker operation but pacemakers do not measure or compute heart signal parameters of the beats in the electrogram signal, nor do they save the computed values of heart signal parameters in memory.

Pacemakers have been used to collect intramyocardial electrogram (IMEG) data for the purpose of using a decrease in electrogram QRS complex voltage as an indicator of the rejection of a transplanted heart. The expense, patient discomfort and inconvenience of endomyocardial biopsy to detect heart transplant rejection makes an electronic method highly desirable. The published paper "Clinical Heart Transplantation without Routine Endomyocardial Biopsy" by Warnecke, et al in the November/December 1992 issue of The Journal of Heart and Lung Transplantation showed that IMEG recordings made with a cardiac pacemaker have the potential to replace endomyocardial biopsy (EMB) as a diagnostic method to detect transplant rejection. Specifically, Warnecke et al showed that an 8% decline in IMEG voltage provided the best sensitivity and specificity as an indicator of potential acute moderate allograft rejection of a transplanted heart. Unfortunately, pacemakers are not designed to collect weeks or months of statistical data on electrogram voltage variations. The additional external support equipment needed to continually offload the raw electrogram data from a pacemaker is expensive and inconvenient to use.

The term "medical practitioner" shall be used herein to mean any person who might be involved in the medical treatment of a patient. Such a medical practitioner would include, but is not limited to, a medical doctor (e.g., a general practice physician, an internist or a cardiologist), a medical technician, a paramedic, a nurse or an electrogram analyst. Although the masculine pronouns "he" and "his" are used herein, it should be understood that the patient or medical practitioner could be a man or a woman. A "cardiac event" includes an acute myocardial infarction, ischemia caused by effort (such as exercise) and/or an elevated heart rate, bradycardia, tachycardia or an arrhythmia such as atrial fibrillation, atrial flutter, ventricular fibrillation, premature ventricular contractions or premature atrial contractions (PVCs or PACs) and the rejection of a transplanted heart.

For the purpose of this invention, the term "electrocardiogram" is defined to be the heart's electrical signal as sensed through skin surface electrodes that are placed in a position to indicate the heart's electrical activity (depolarization and repolarization). An electrocardiogram segment refers to electrocardiogram data for either a specific length of time, such as 10 seconds, or a specific number of heart beats, such as 10 beats. For the purposes of this specification, the PQ segment of a patient's electrocardiogram is the typically flat segment of a beat of an electrocardiogram that occurs just before the Q and R waves. For the purposes of this specification the ST segment of a patient's electrocardiogram is that segment of a beat of an electrocardiogram that occurs just after the S wave.

Although occasionally described as an electrocardiogram (ECG), the electrical signal from the heart as measured from electrodes within the body is properly termed an "electrogram" or intramyocardial electrogram (IMEG). For the purpose of this invention, the term "electrogram" is defined to be the heart's electrical signal from one or more implanted electrode(s) that are placed in a position to indicate the heart's electrical activity (depolarization and repolarization). An "electrogram segment" refers to a recording of electrogram data for either a specific length of time, such as 10 seconds, or a specific number of heart beats, such as 10 beats. For the purposes of this specification the PQ segment of a patients electrogram is the typically flat, generally horizontal segment of an electrogram that occurs just before the Q and R waves. For the purposes of this specification the ST segment of a patient's electrogram is that segment of an electrogram that occurs just after the S wave. For the purposes of this specification, the term QRS voltage is defined as a measure of QRS complex voltage amplitude which may either be measured from Q to R, or S to R of a beat of the electrogram. For the purposes of this specification, the term QRS segment or QRS complex is that segment of the electrogram from the Q through the R and ending at the J point of the S wave. For the purposes of this specification, the terms "detection" and "identification" of a cardiac event have the same meaning. A beat is defined as a sub-segment of an electrogram or electrocardiogram segment which covers the electrical signal from the heart for exactly one beat of the heart and includes exactly one R wave. If the heart rate is 60 bpm, then the sub-segment of the electrogram that is exactly one beat would represent a sub-segment of the electrogram that is exactly 1.0 second in duration. For the purposes of this invention, the term "average value", "average amplitude" or "average voltage" of any segment (viz., QRS complex, ST segment or PQ segment) of the electrogram shall be defined as meaning either the mean or the median of a multiplicity of measurements of that segment. It is also envisioned that in some cases both mean and median may be computed and will on occasion be described separately herein.

"Heart signal parameters" are defined to be any measured or calculated value created during the processing of one or more beats of electrogram (or electrocardiogram) data. Heart signal parameters are features of the electrogram derived from one or more measured values and include PQ segment average voltage, ST segment average voltage, R wave peak voltage, ST deviation (ST segment average voltage minus PQ segment average voltage), ST shift (ST deviation compared to a baseline average ST deviation taken at some prior time), average signal strength, T wave peak height, T wave average voltage, T wave deviation, QRS complex width, QRS voltage, heart rate and R-R interval. Counts of the number of arrhythmia related events such as PACs, PVCs and/or episodes of atrial fibrillation are not considered herein to be heart signal parameters as they do not directly result from a measured value derived from a beat of the electrogram. ST segment related heart signal parameters include, ST segment average voltage, ST deviation and ST shift.

SUMMARY OF THE INVENTION

A "tracker system" as defined herein includes implanted electrical leads which are part of an implanted cardiotracker plus external equipment that includes external alarm means and a physician's programmer. The present invention is the tracker system for monitoring the degradation of a patient's cardiovascular condition from one or more causes. These causes include the rejection of a transplanted heart and further include the progression of a stenosis in a coronary artery; e.g., as one or more stenoses in a coronary artery become progressively more narrow thereby causing reduced blood flow to the heart muscle. As less and less blood is available to the heart muscle, the patient's ST segment will shift during exertion by an ever increasing amount. Eventually, if the stenosis severely restricts blood flow or a plaque rupture occurs, a thrombus can form causing an AMI. By noting changes over time in the shift of ST segment voltage in relation to the patient's heart rate, the patient's doctor can identify coronary artery narrowing and intervene before a potentially fatal AMI occurs. The preferred intervention for such narrowing is the implantation of one or more drug eluting stents to restore normal blood flow for the coronary circulation. The tracker system also has the capability for tracking electrogram signal amplitude (e.g., QRS voltage) as well as electrogram feature time durations such as the width of the QRS complex, etc. A decrease in the average value of the QRS voltage as compared to a baseline value for that parameter has been shown to be an early indicator of rejection of a transplanted heart. By careful monitoring of this heart signal parameter, the number of periodic biopsies of heart tissue as an indicator of transplant rejection can be greatly reduced which provides a significant cost savings as well as a reduction in the myocardial scar tissue created by each biopsy.

As previously stated, the tracker system includes a device called a cardiotracker for processing and recording patient heart electrical signals, a physician's programmer and an external alarm system. In the preferred embodiment of the present invention, the cardiotracker is implanted along with the leads that have electrodes that can sense the heart's electrogram. In an alternative embodiment, the cardiotracker including the electrodes could be external but attached to the patient's body. Although the present invention (as described herein) in most cases refers to the preferred embodiment of an implanted cardiotracker which can process electrogram data from implanted electrodes, the techniques described are equally applicable to an alternative embodiment where an external cardiotracker processes electrocardiogram data from appropriately placed skin surface electrodes.

In the preferred embodiment of the cardiotracker, either or both subcutaneous electrodes or electrodes located on a pacemaker type right ventricular or atrial leads can be used. It is also envisioned that one or more electrodes may be placed within the superior vena cava or other vessels of the circulatory system. One version of the implanted cardiotracker device using subcutaneous electrodes would have an electrode located under the skin on the patient's left side. This could be best located between 2 and 20 inches below the patient's left arm pit. The cardiotracker case acting as the indifferent electrode would typically be implanted like a pacemaker under the skin on the upper left side of the patient's chest. Still another version of the cardiotracker could utilize epidural electrodes attached externally to the heart. This attachment of epidural electrodes to the exterior surface of the heart from an epidural lead could take place during the surgery for a transplanted heart.

The physician's programmer is used to program the cardiotracker with respect to any or all of its diagnostic, detection, alarming and alerting functions. The physician's programmer is also used to retrieve and analyze recorded electrogram segments and other processed heart signal data from the cardiotracker memory.

Such processed heart signal parameter data includes histograms and statistical data that can be used to identify changes in cardiovascular condition over time periods of days, weeks, months or even years. The histogram data can be analyzed by the patient's physician using analysis tools provided in the physician's programmer. The histogram and/or average value data can also be compared against preset thresholds that are programmed into the cardiotracker. If the thresholds are exceeded, the cardiotracker can activate internal and/or external alarm means for alerting the patient to seek medical attention.

Of particular importance is the ability of the histograms in the cardiotracker to track QRS complex voltage amplitude (or simply the QRS voltage) on a daily basis. While QRS complex peak-to-peak voltage is the preferred measurement used for QRS voltage, other signal amplitudes such as PQ segment to R height or S wave amplitude are also envisioned. A current publication "Clinical Heart Transplantation Without Routine Endomyocardial Biopsy" by Warnecke et al in The Journal of Heart and Lung Transplantation showed that intramyocardial electrogram (IMEG) recordings made with a cardiac pacemaker have the potential to replace endomyocardial biopsy (EMB) as a diagnostic means to detect transplant rejection. Specifically, Warnecke et al showed that an 8% decline in electrogram voltage provided the best sensitivity and specificity as the indicator of potential acute moderate allograft rejection.

While pacemakers are not designed to collect weeks or months worth of statistical data on electrogram voltage variations, the present invention cardiotracker and tracker system is ideally suited for that purpose. A daily histogram stored in cardiotracker memory which tracks the electrogram voltage for every beat analyzed, (e.g., 3 to 12 beats every 30 seconds) can provide the data needed to identify potential transplant rejection without the need for endomyocardial biopsy. The histogram data would be downloaded to the tracker system's physician's programmer for analysis allowing the medical practitioner to identify a drop in electrogram voltage indicative of transplant rejection. Specifically, a decrease in the average value of a multiplicity of recently measured QRS voltages compared to a baseline QRS voltage taken when the transplanted heart was not being rejected can be used by the cardiotracker to detect the early rejection of a transplanted heart. This detection can also be used to initiate a patient alert warning signal to advise the patient to seek medical attention. By changing medications as to type or amount, the rejection of the heart transplant can be reversed and the patient's life can be saved. It also may be desirable that the cardiotracker or tracker system programmer be capable of calculating the average (i.e., mean or median) and standard deviation of the distribution of the multiplicity of measured QRS voltages captured by a histogram data storage technique. For example a reduction of greater than 8% of the daily mean QRS voltage compared to a baseline value for this parameter could be an important indicator of transplant rejection. It is also envisioned that the average QRS voltage over a preset data collection time period (e.g., a day) could be collected by a cardiotracker without the need for a histogram.

The cardiotracker histogram capability could also track electrogram segment voltages as a function of heart rate creating two or more histograms per day where each histogram represents the distribution of QRS voltage for every beat in a pre-specified heart rate range. Furthermore, the cardiotracker could be programmed to record the QRS complex voltage only during a limited time period. It may be preferable to select a time period when the patient would normally be sleeping such as from midnight to 5 AM.

Similar to the cardiosaver device described by Fischell et al in U.S. Pat. Nos. 6,112,116, 6,272,379 and 6,609,023, which are incorporated herein by reference, the cardiotracker can detect an acute change in the patient's electrogram that is indicative of a cardiac event, such as an acute myocardial infarction, within five minutes after it occurs and then automatically warn the patient that the event is occurring. To provide this warning, the tracker system includes an internal alarm sub-system (internal alarm means) within the cardiotracker and/or an external alarm system (external alarm means). In the preferred embodiment, the cardiotracker communicates with the external alarm system using a wireless radio-frequency (RF) signal. It is envisioned that the external alarm system of the tracker system would have capabilities equivalent to those described by Fischell et al in U.S. Pat. Nos. 6,112,116, 6,272,379 and 6,609,023.

As in the Fischell et al devices as previously described, it is envisioned that there would be at least two types of alarms: a major/critical event alarm (an "EMERGENCY ALARM") signaling the detection of a major cardiac event (e.g., a heart attack which is an AMI) and the need for immediate medical attention, and a less medically significant alert (a "SEE DOCTOR ALERT" or alarm) signaling the detection of a less serious condition that is not life threatening such as exercise induced ischemia resulting from a stenosis that is limiting blood flow in a coronary artery. Detection of a decreased QRS voltage indicative of the rejection of a transplanted heart could most appropriately be indicated by a SEE DOCTOR ALERT because this is not an emergency situation but rather one which should inform the patient to see a doctor as soon as convenient.

It is also envisioned that the external alarm system of the tracker system would have capabilities equivalent to that described by Fischell et al in U.S. Pat. Nos. 6,112,116, 6,272,379 and 6,609,023.

Techniques to capture electrogram data and heart signal parameter data computed from electrograms over days, weeks or months are important because, as discussed above, some of the processes of heart malfunction are gradual and it is desirable to detect and treat such conditions before the onset of an acute event such as an AMI or ventricular fibrillation or the complete rejection of a transplanted heart. Limiting the amount of memory and electrical power needed in the implanted cardiotracker to collect, store and analyze the electrogram data looking for trends is especially important in implantable and portable systems.

The present invention cardiotracker will compute the value of one or more heart signal parameters for each of a multiplicity of beats of the electrogram. These values will be stored in memory for a first time period which is defined as the "data collection time period." The cardiotracker would typically store these values of the one or more heart signal parameters for a multiplicity of data collection time periods over a second time period which is defined as the "collected data retention time period." The cardiotracker would typically compute extracted heart signal parameters (e.g., the mean or median value) extracted from the heart signal parameter values stored in memory during each data collection time period. The cardiotracker would typically store the values of extracted heart signal parameters for a third time period defined as the "extracted data retention time period." In the preferred embodiment of the present invention, the values of the one or more heart signal parameters stored during the data collection time period would be stored as a histogram or histograms.

The present invention cardiotracker can track any combination of the following heart signal parameters:
1. ST segment voltage
2. ST deviation (ST segment amplitude-PQ segment amplitude for a single heart beat),
3. R-R interval (time period between successive R waves),
4. R-R interval variability,
5. R peak height,
6. R wave width
7. QRS voltage,
8. QRS width,
9. RS width,
10. T wave width and/or amplitude,
11. T wave alternans, and
12. QRS shift (a recent average value of QRS voltage over a data collection time period minus the baseline QRS voltage where baseline QRS voltage is the average value of the QRS voltage for a multiplicity of heart beats at a time when the heart of a heart transplant patient is not undergoing rejection)

The present invention cardiotracker can also count arrhythmia related events (that are not heart signal parameters) including:
a) incidence of PACs or PVCs
b) PVC beats per electrogram segment,
c) occurrences of two consecutive beats that each have a PVC,
d) the incidence and duration of episodes of ventricular tachycardia,
e) occurrences of three consecutive PVCs and/or
f) the incidence and time duration of episodes of atrial fibrillation.

Some of these data will be predictive of ventricular fibrillation. For example, if there is a change in the frequency of beats with a heart signal parameter that is indicative of a forthcoming episode of ventricular fibrillation, then certain medication may be prescribed or an implantable cardioverter defibrillator (ICD) could be implanted.

In one preferred embodiment of the present invention cardiotracker, the above mentioned heart signal parameters and/or counts of arrhythmia related events are tracked using a histogram technique.

The dictionary defines a histogram as a "representation of a frequency distribution by means of rectangles whose widths represent class intervals and whose areas are proportional to the corresponding frequencies". The present invention cardiotracker is designed to create histograms to track the frequency distribution of beats (number of beats in a preset time period) having heart signal parameter levels within a multiplicity of pre-specified ranges (class intervals). Such a histogram could be displayed by the physician's programmer as a bar chart (a collection of rectangles) where the width of each bar represents a single pre-specified range (class interval) of a heart signal parameter and the area of the bar (height.times. width) is proportional to the number of beats (corresponding frequency) in that range of the heart signal parameter. The preferred embodiment of the present invention uses a uniform width (pre-specified range) for each bar and has the height of the bar equal to the number of beats in the data collection time period having that one heart signal parameter within that pre-specified range. As an example, in the heart rate range of 50 to 80 beats per minute (bpm), the height of a particular bar could indicate that in the data collection time period of 24 hours, there were 3,005 beats having a measurement of QRS voltage between 96% and 98% of the baseline QRS voltage that was measured during a period of 24 hours at 10 days after the heart transplant surgery when biopsy showed no indications of rejection. In a preferred embodiment of the present invention the QRS voltage range of 96% to 98% of baseline would also be expressed as the percent deviation from baseline QRS voltage of −4% to −2%.

The histograms of the present invention can be used to aid the medical practitioner in determining if a patient is developing a potentially dangerous heart condition. As far as the detection of ischemia (including detection of AMI) is concerned, the tracker system as described herein could accurately be called an "Ischemia Management System" or IMS. The use of such histograms will be clarified with the assistance of FIGS. 6A, 6B, 7A and 7B as provided below in the DETAILED

DESCRIPTION OF THE INVENTION

In addition, the present invention cardiotracker could provide a set of histograms where each histogram represents a range of a first heart signal parameter and the class intervals of each histogram represent pre-specified ranges of a second heart signal parameter. For example, a first heart signal parameter would be the R-R interval for the beat and the second heart signal parameter would be the ST deviation. It is also envisioned that the cardiotracker would contain a multiplicity of histogram sets where each set would represent the data collected from a different time period (e.g., if the data collection time period is a day, then 7 sets are needed for a week and that week would be the collected data retention time period).

Furthermore, the implanted cardiotracker can process the histogram(s) to compute extracted histogram data such as:
1. the median ST deviation for each histogram,
2. the histogram bin having the highest value for a specific parameter,
3. The mean value of ST deviation for each histogram,
4. the standard deviation of the histogram distribution with respect to the highest value bin or with respect to the mean or median,
5. The number of beats per day per histogram exceeding a pre-specified threshold of ST deviation,
6. The moving average over two or more data collection time periods of any of items 1 through 5,
7. The median of the QRS or RS width histogram, and
8. The average (mean and/or median) QRS voltage over a pre-specified time period and/or within a certain range of heart beats per minute.
9. The QRS shift which is the average QRS voltage over a data collection time period compared to the baseline QRS voltage. QRS shift is typically the average QRS voltage given as a percentage deviation from the baseline QRS voltage.

If number 5 above is used, suggested values for each pre-specified ST deviation histogram threshold could be calculated by the programmer based on previously collected histogram data.

The extracted histogram data can then be compared by the cardiotracker with a detection threshold. If the threshold is exceeded, the cardiotracker can take one or more actions including alerting the patient by means of a SEE DOCTOR ALERT. It is also envisioned that the cardiotracker could compare changes in extracted data between two time periods to detect a change that warrants alerting the patient.

Examples of use of these histograms for the present invention are as follows:

1. For each beat it processes, the cardiotracker would typically compute three heart signal parameters, the ST deviation (i.e., average ST segment signal level minus average PQ segment signal level), the QRS voltage and the R-R interval which is the time between heart beats whose inverse is a measure of heart rate. The QRS voltage might be computed only during a programmed period each day (e.g., during sleep) while the ST deviation would typically be monitored all the time.

2. a. The cardiotracker memory would have a current section containing a set of five ST deviation histograms, where each of the five histograms corresponds to a different range of heart rate (i.e., five different R-R intervals). Each ST deviation histogram has (for example) 25 bins where each bin acts as a counter for the number of beats having an ST deviation within a specific range. That specified range has previously been termed the "class interval". An example of the specific range or class interval for ST deviation might be between −7.5% and −2.5% of the amplitude of the average baseline ST deviation taken at approximately the same time on the prior day b. The cardiotracker memory would also have a current section containing two or three QRS voltage histograms, where each of the QRS voltage histograms corresponds to a different range of heart rates (i.e., different R-R intervals). Each QRS voltage histogram has (for example) 25 bins where each bin acts as a counter for the number of beats having a QRS voltage within a specific range.

3. The value of the R-R interval computed in (1) above will be used by the cardiotracker to select one of the five ST deviation histograms (2a) into which the ST deviation data for the beat is placed, and one of the QRS voltage histograms (2b) into which the QRS voltage data for the beat is placed. That is, an R-R interval of 1.0 second corresponds to a heart rate of 60 bpm. Therefore, if the R-R interval is 1.0 second, data on a particular heart signal parameter would be placed in that specific histogram for heart rates between 50 and 80 bpm.

4. The value of ST deviation computed in (1) above will then be used to pick and increment by one, one of the bins within the selected ST deviation histogram where the value of ST deviation of the beat lies within the range of ST deviation associated with that specific bin. The value of QRS voltage computed in (1) above will then be used to pick and increment by one, one bin within the selected QRS voltage histogram where the value of QRS voltage of the beat lies within the range of QRS voltage associated with that specific bin.

It is also envisioned that instead of a single histogram per data collection time period, there might be a set of histograms allowing the cardiotracker to track the first heart signal parameter (e.g., those listed above) for different ranges of a second heart signal parameter. For example, QRS voltage might be tracked in a set of three different histograms where each of the three histograms in the set corresponds to a different range of R-R interval or heart rate. Furthermore, these data can be tracked where each histogram (or histogram set) represents a time period as short as a minute to as long as several years. Similarly, many histograms or histogram sets corresponding to successive data collection time periods may be stored in the cardiotracker and/or programmer to allow the physician to follow the long term cardiovascular condition of the patient.

In a preferred embodiment of the present invention, a multiplicity of histogram sets would track the frequency distribution of beats with respect to two heart rate parameters where each set would correspond to one day. Eight sets would be contained in memory to provide one set for the current day and seven sets corresponding to the previous seven days.

Additional memory for extracted histogram data would hold basic and/or processed extracted data for each histogram in each set for each day for as long as a year. This provides tremendous data compression. For example, with only 2 kilobytes of memory, the cardiotracker memory could store any of the following types and amounts of data:

1. 10 seconds of electrogram data at 200 samples per second, or 2. 8 days of histogram data in 5 different heart rate ranges with 25 bins per histogram, or 3. 6 months of the average value of a heart signal parameter (viz., the average value of the QRS voltage within a particular range of heart rates)., and number of beats in each day's histograms from (2) above.

For the purpose of this disclosure, the term "data collection time period" is defined as the time during which the cardiotracker will be updating a histogram or histogram set. The data collection time period could be as short as a minute and as long as many months. Ideally, collection on a daily basis would provide important information and would minimize effects from daily cycles. A data collection time period of less than an hour would be useful to collect ST deviation vs. heart rate data during a stress test in the doctor's office. The data collected during such a stress test could be compared to earlier stress tests using analysis tools built into the physician's programmer of the tracker system. In this way the doctor could detect an increased level of coronary ischemia which may be caused by progressive narrowing of one or more coronary arteries.

The "collected data retention time period" is hereby defined as the time period over which a histogram or histogram set is stored in cardiotracker memory before it is overwritten with new data. For example if the data collection time period is one day and there are 8 sections of histogram memory (each corresponding to a day), then one section will be the current day with histogram stored from the 7 previous days thus the collected data retention time period is 7 days. The "extracted data retention time period" is similarly defined as the time period over which the extracted histogram data is stored in cardiotracker memory before it is overwritten with new data. For example, if the extracted histogram data (median ST deviation and number of counts) are extracted at the end of each day from that day's histogram, and each day's value of extracted data is stored in cardiotracker memory for 6 months before it is overwritten with new data, then the extracted data retention time period is 6 months.

Important aspects of the present invention are the techniques used by the physician's programmer to display the collected histogram data to allow a physician to clearly see trends in his patient's cardiovascular condition. These displays include:

1. a screen including bar charts separately showing each of the histograms in a set of histograms for one or more data collection time periods (e.g., one or more days). For example, the five ST deviation histograms corresponding to five different heart rate ranges form a set of histograms and QRS voltage histograms for two or three different heart rate ranges form a set of QRS voltage histograms, 2. a screen that shows line graphs combining all of the histograms in a set of histograms for one or more data collection time periods where each histogram in the set is represented by a different line, Each line being either a different pattern (e.g. solid line, dashed line, dotted line, etc.) or a different color for a line.

3. a screen including the line graphs of item 2 for more than one data collection time period where a typical data collection time period is one day, and 4. a screen including a line graph of one or more types of extracted histogram data as a function of time (e.g., the QRS shift) plotted each day for a period of 6 months where the 6 months is the extracted data retention time period).

The physician's programmer would also be used by the physician to define or select the heart signal parameters that will be tracked using the histogram technique. It is also envisioned that the physician's programmer will be able to process the histogram data downloaded from the patient's cardiotracker to suggest detection thresholds for the detection by the cardiotracker of future cardiac events that warrant patient alerting or alarming.

An important part of the concept of the present invention is the comparison of a recent value for some heart signal parameter with a baseline value for that parameter that was measured at a prior time. The baseline value would typically be an average value of the heart signal parameter collected over a pre-specified period of time, e.g., the data collection time period.

For example, while it is envisioned that the cardiotracker might measure the QRS voltage for each beat and use the actual measured QRS voltage values to populate QRS voltage histograms, a preferred embodiment of the present invention would track the QRS voltage for each beat as a percentage of baseline QRS voltage or preferably as the percent deviation (change) from the baseline QRS voltage. In a preferred embodiment of the present invention, the histograms would therefore track the percentage deviation from baseline QRS voltage. Similarly, the average QRS voltage for each data collection time period would be tracked as a percentage deviation from the baseline QRS voltage. Average QRS voltage for each data collection time period is an example of extracted histogram data that would be stored in the extracted histogram data memory of the cardiotracker. For example, the cardiotracker could calculate the baseline QRS voltage being the average value of the QRS voltage for one day at a time after a heart was transplanted into a human subject when traditional medical testing showed that the heart is not being rejected. This would serve as the "baseline QRS voltage" against which all future QRS voltage measurements would be compared. The useful concept here being that a significant decline of the current QRS voltage compared to the baseline QRS voltage would indicate that the transplanted heart is being rejected.

For example, each day after the baseline QRS voltage is obtained, the value of the day's average QRS voltage (either as measured or as a percent deviation from the baseline QRS voltage) would be placed in the computer memory of the cardiotracker. This would be the "recent" average QRS voltage. The cardiotracker would be designed to detect transplant rejection when the deviation between the recent average QRS voltage compared to the baseline QRS voltage exceeds a preset threshold. Thus, if the recent daily average QRS voltage was less than the baseline QRS voltage by more than (let us say) 8%, the cardiotracker would detect rejection. If enabled, the patient alerting function of the cardiotracker would then initiate a SEE DOCTOR ALERT to be triggered from either or both an internal alarm means and/or an external alarm means. This alarm would alert the patient to seek medical attention in a timely manner, hopefully, to save the patient's life.

While it may be sufficient to detect transplant rejection when the deviation of average daily QRS voltage as compared to the baseline QRS voltage exceeds a preset threshold for a single day, it may be more reliable to require that the threshold be exceeded for two or more sequential days.

Thus it is an object of this invention is to have a tracker system including a cardiotracker designed to track slow changes in the condition of the patient's heart.

Another object of the present invention is to have a tracker system including a cardiotracker designed to track one or more heart signal parameters through the use of stored histograms.

Still another object of the present invention is to have a cardiotracker capable of comparing basic or processed extracted histogram data with a physician-set threshold and alerting the patient when that threshold is crossed.

Still another object of the present invention is to have a cardiotracker that can calculate a moving average of extracted histogram data over relevant time periods and use the moving average to track the condition of the patient's heart.

Still another object of the present invention is to have the physician's programmer process downloaded histogram and extracted histogram data from the cardiotracker to suggest detection thresholds for acute cardiac event detection by the cardiotracker.

Still another object of the present invention is to have the cardiotracker determine average values for QRS voltage over a data collection time period and also have the capability to provide a SEE DOCTOR ALERT if that average value of the QRS voltage deviates from a baseline QRS voltage by more than a preset amount for one or more sequential data collection time periods.

Yet another object of the present invention is to have a cardiotracker store QRS voltage as a percentage of the baseline QRS voltage.

Yet another object of the present invention is to have a cardiotracker store QRS voltage as a percentage deviation from the baseline QRS voltage.

Yet another object of the present invention is to have a cardiotracker compute the average QRS voltage over a data collection time period as a percentage deviation from the baseline QRS voltage, which percentage deviation is the QRS shift.

These and other objects and advantages of this invention will become obvious to a person of ordinary skill in this art upon reading of the detailed description of this invention including the associated drawings as presented herein.

DETAILED DESCRIPTION OF THE INVENTION

Figure 1:
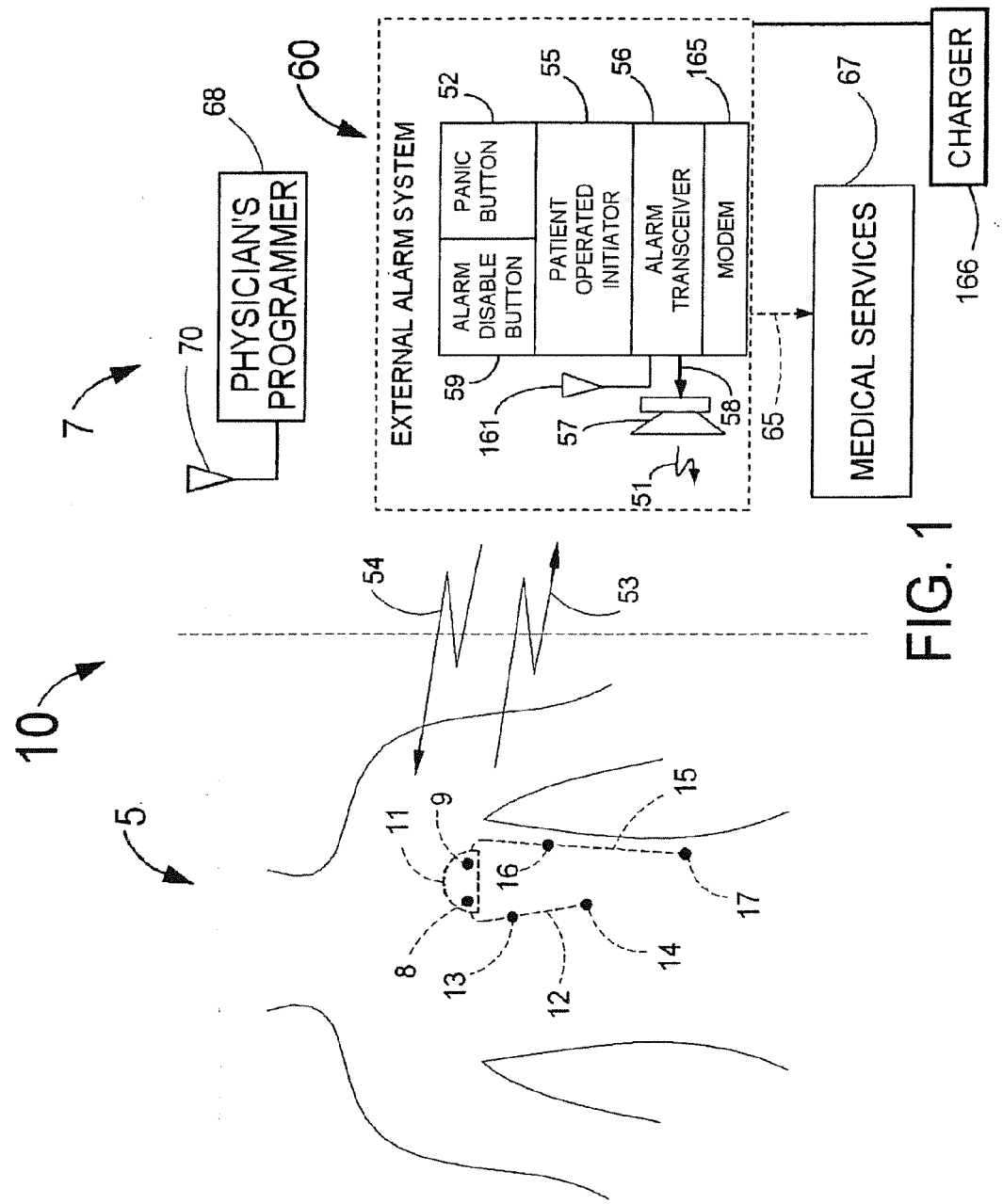
FIG. 1 illustrates a tracker system for the detection of a cardiac event and for warning the patient that a cardiac event is occurring.

FIG. 1 illustrates an example of a tracker system 10 including an implanted cardiotracker 5 and external equipment 7. The cardiotracker 5 includes electrical wire leads 12 and 15 and a battery-powered electronics module contained within a metal case 11. The cardiotracker 5 can track the patient's cardiovascular condition over extended periods of time. The cardiotracker 5 can also detect acute cardiac events including acute myocardial infarction and arrhythmias and warn the patient when such an event occurs. The cardiotracker 5 can also track slowly changing cardiac functions such as day-to-day changes in QRS voltage that can be indicative of the rejection of a transplanted heart. The cardiotracker 5 can record the patient's electrogram signal for later review by a medical practitioner. The cardiotracker 5 can capture histogram-based historical representations of one or more heart signal parameters for later analysis and review by a medical practitioner. The cardiotracker 5 can also send out wireless signals 53 to and receive wireless signals 54 from the external equipment 7. The functioning of the cardiotracker 5 will be explained in greater detail with the assistance of FIGS. 2, 3, 4 and 5.

The cardiotracker 5 has two leads 12 and 15 that have one or more electrical conductors (wires) with surrounding insulation. The lead 12 is shown with two electrodes 13 and 14. The lead 15 has subcutaneous electrodes 16 and 17. In fact, the cardiotracker 5 could utilize as few as one lead or as many as three and each lead could have as few as one electrode or as many as eight electrodes. Furthermore, electrodes 8 and 9 could be placed on the outer surface of the case 11 without any wire leads extending from the cardiotracker 5.

The lead 12 in FIG. 1 could advantageously be placed through the patient's vascular system with the electrode 14 being placed into the apex of the right ventricle. The lead 12 with electrode 13 could be placed in the right ventricle or right atrium or the superior vena cava similar to the placement of leads for pacemakers and implantable cardioverter defibrillators (ICDs). The metal case 11 of the cardiotracker 5 could serve as an indifferent electrode with either or both electrodes 13 and/or 14 being active electrodes. It is also conceived that the electrodes 13 and 14 could be used as bipolar electrodes. Alternately, the lead 12 in FIG. 1 could advantageously be placed through the patient's vascular system with the electrode 14 being placed into the apex of the left ventricle. The electrode 13 could be placed in the left atrium.

The lead 15 could advantageously be placed subcutaneously at any location where the electrodes 16 and/or 17 would provide a good electrogram signal indicative of the electrical activity of the heart. Again for this lead 15, the case 11 of the cardiotracker 5 could be an indifferent electrode and the electrodes 16 and/or 17 could be active electrodes or electrodes 16 and 17 could function together as bipolar electrodes. The cardiotracker 5 could operate with only one lead and as few as one active electrode with the case 11 of the cardiotracker 5 being an indifferent electrode. The tracker system 10 described herein can readily operate with only two electrodes. It is also envisioned that the lead 15 could be an epicardial lead with the electrode 17 being firmly attached to the heart muscle from outside of the patient's heart and the electrode 13 being implanted elsewhere within the patient's body.

One embodiment of the cardiotracker device 5 using subcutaneous lead 15 would have the electrode 17 located under the skin on the patient's left side. This could be best located between 2 and 20 inches below the patient's left arm pit. The cardiotracker case 11 could act as the indifferent electrode and would typically be implanted under the skin on the upper left side of the patient's chest. Alternately, both electrodes 8 and 9 could, like the Medtronic Reveal™, be located on the surface of the cardiotracker case 11.

FIG. 1 also shows the external equipment 7 that consists of a physician's programmer 68 having an antenna 70 and an external alarm system 60 including a charger 166 that could be used to charge a rechargeable battery (not shown) in the external alarm system 60. It should be understood that the external alarm system 60 could also be powered by a conventional (i.e., non-rechargeable) battery. The external equipment 7 provides means to interact with the implanted cardiotracker 5. These interactions include programming the cardiotracker 5, retrieving data collected by the cardiotracker 5 and handling alarms generated by the cardiotracker 5.

The purpose of the physician's programmer 68 shown in FIG. 1 is to set and/or change the operating parameters of the implantable cardiotracker 5 and to read out data stored in the memory of the cardiotracker 5 such as stored electrogram segments, histograms and extracted histogram data. This would be accomplished by transmission of a wireless signal 54 from the programmer 68 to the cardiotracker 5 and receiving of telemetry by the wireless signal 53 from the cardiotracker 5 to the programmer 68. When a laptop computer is used as the physician's programmer 68, it would require connection to a wireless transceiver for communicating with the cardiotracker 5. Such a transceiver could be connected via a standard interface such as a USB, serial or parallel port or it could be inserted into the laptop's PCMCIA card slot. The screen on the laptop physician's programmer 68 would be used to provide guidance to the medical practitioner in communicating with the cardiotracker 5. Also, the screen could be used to display both real time and stored electrograms that are read out from the cardiotracker 5 as well as histograms and extracted data based on any one of several heart signal parameters.

In FIG. 1, the external alarm system 60 has a patient operated initiator 55, an alarm disable button 59, a panic button 52, an alarm transceiver 56, a speaker 57, a modem 165 and an antenna 161. The modem 165 allows data transmission to and from medical services 67 via the communication link 65. It is also envisioned (but not shown in FIG. 1) that the external alarm system 60 could include a microphone and associated electronics for two-way voice communication with the medical services 67.

If a cardiac event is detected by the cardiotracker 5 or the long term cardiovascular tracked data has exceeded a programmed limit, an alarm message is sent by a wireless signal 53 to the alarm transceiver 56 via the antenna 161. When the alarm message is received by the alarm transceiver 56, a signal 58 is then sent to the loudspeaker 57. The signal 58 will cause the loudspeaker 57 to emit an external audio alarm signal 51 to warn the patient that an event has occurred. Examples of external alarm signals 51 include a periodic buzzing, a sequence of tones and/or a speech message that instructs the patient as to what is happening and what actions should be taken. Furthermore, the alarm transceiver 56 can, depending upon the nature of the signal 53, can send an outgoing signal over the link 65 to contact emergency medical services 67. When the detection of an acute myocardial infarction or other life threatening cardiac event (e.g., tachycardia) is the cause of the alarm, the alarm transceiver 56 could automatically notify medical services 67 that a serious cardiac event has occurred and an ambulance could be sent to treat the patient and to bring him to a hospital emergency room or directly to a catheterization laboratory.

If communication with medical services 67 is enabled and a cardiac event alarm is sent within the signal 53, the modem 165 will establish the data communications link 65 over which a message will be transmitted to the medical services 67. The message sent over the link 65 may include any one, a combination of several or all of the following information types: (1) a specific patient is having an acute myocardial infarction or other cardiac event, (2) the patient's name, address and a brief medical history, (3) a map and/or directions to where the patient is located (using the GPS satellite or cellular location means is also envisioned), (4) the patient's stored electrogram including baseline electrogram data and the specific electrogram segment that generated the alarm (5) continuous real time electrogram data, and (6) a prescription written by the patient's personal physician as to the type of treatment and/or the amount of drug to be administered to the patient in the event of a specific cardiac event. If the medical services 67 include an emergency room at a hospital, information can be transmitted that the patient has had a cardiac event and should be on his way to the emergency room. In this manner the medical practitioners at the emergency room and/or a catheterization laboratory could be prepared for the patient's arrival.

Just as the ONSTAR™ service will respond to help a driver immediately after a car's air bags deploy, so might the medical services 67 respond to the patient upon receipt of information that a serious cardiac event has occurred. Such a serious cardiac event would cause an EMERGENCY ALARM signal to be initiated by the internal alarm means in the cardiotracker and (if within range) an external alarm would sound from the external alarm system 60. Based on the patient's cardiac event and prior instructions from the patient's physician, the medical services personnel can instruct the patient and summon appropriate help.

The purpose of the patient operated initiator 55 is to give the patient the capability for initiating transmission of captured electrogram segments and histogram data from the cardiotracker 5, through the external alarm system 60, to a medical practitioner at the medical services 67. This will enable one or more electrogram segments to be displayed for a medical practitioner. The alarm disable button 59 can be used by the patient to turn off the internal alarm signal generated within the cardiotracker 5 and/or turn off the external alarm signal 51 played through the speaker 57. If the alarm disable button is not pressed, either or both the internal and external alarms would continue for a preset period of time such as 15 minutes. A reminder alarm signal might then be triggered at some later time (e.g., 2 to 5 hours later) if the patient has not turned off the alarms by means of the alarm disable button 59.

The patient might press the panic button 52 in the event that the patient feels that he is experiencing a cardiac event even if there is no alarm signal from either the internal or external alarm means. The panic button 52 will initiate the transmission from the cardiotracker 5 to the external alarm system 60 via the wireless signal 53 of both recent and baseline electrogram segments. Also, following the use of the panic button 52, the tracker system 10 can be programmed to transmit the last set of histograms tracking a particular aspect of the patient's cardiovascular condition. In addition, an analysis of the histogram data, for example, the 5 day moving average of a heart signal parameter (e.g., ST deviation) over the last week or month, may be transmitted to medical practitioners at the medical services 67 to allow them to see trends in the patient's cardiovascular condition. The external alarm system 60 will then retransmit these data via the link 65 to medical services 67 where a medical practitioner will view the data. The medical practitioner remotely located at the medical services 67 could then analyze the data and call the patient back to offer advice as to whether this is an emergency situation or the situation could be routinely handled by the patient's personal physician at some later time.

Figure 2:
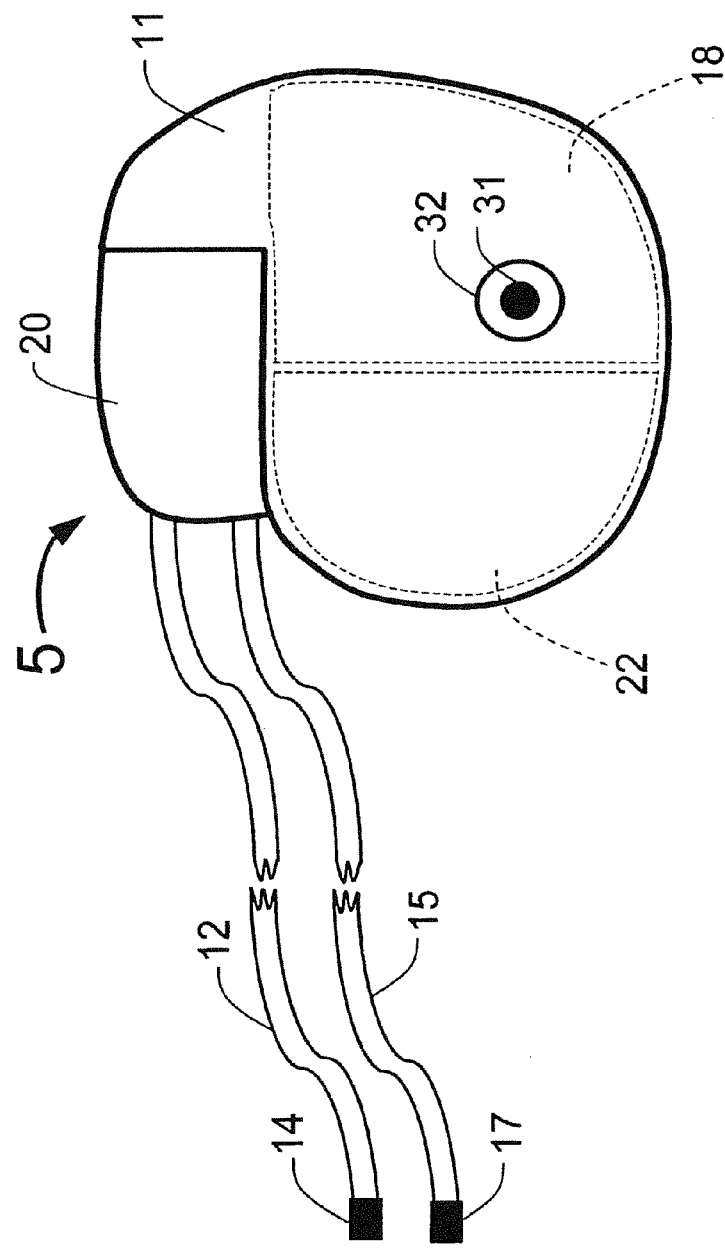
FIG. 2 is a plan view of an implantable cardiotracker showing the cardiotracker electronics module and two electrical leads each having one electrode.

FIG. 2 is a plan view of the cardiotracker 5 having a metal case 11 and a plastic header 20. The case 11 contains the battery 22 and the electronics module 18. This type of package is well known for pacemakers, implantable defibrillators and implantable tissue stimulators. Electrical conductors placed through the plastic header 20 connect the electronics module 18 to the electrical leads 12 and 15, which have respectively electrodes 14 and 17. The lead electrodes 13 and 16 and the on-case electrodes 8 and 9 of FIG. 1 are not shown in FIG. 2. It should also be understood that the cardiosaver 5 can function with only two electrodes, one of which could be the case 11. All the different configurations for electrodes shown in FIGS. 1 and 2, such as the electrodes 8, 9, 13, 14, 16 or the metal case 11 are shown only to indicate that there are a variety of possible electrode arrangements that can be used with the cardiosaver 5.

On the metal case 11, a conducting disc 31 mounted onto an insulating disc 32 can be used to provide a subcutaneous electrical tickle to warn the patient with a SEE DOCTOR ALERT or an EMERGENCY ALARM or the disc 31 could act as an independent electrode for sensing the patient's electrogram. Alternatively, the electrode 8 or the electrode 9 of FIG. 1 could be used as a sensing electrode for the electrogram.

Figure 3:
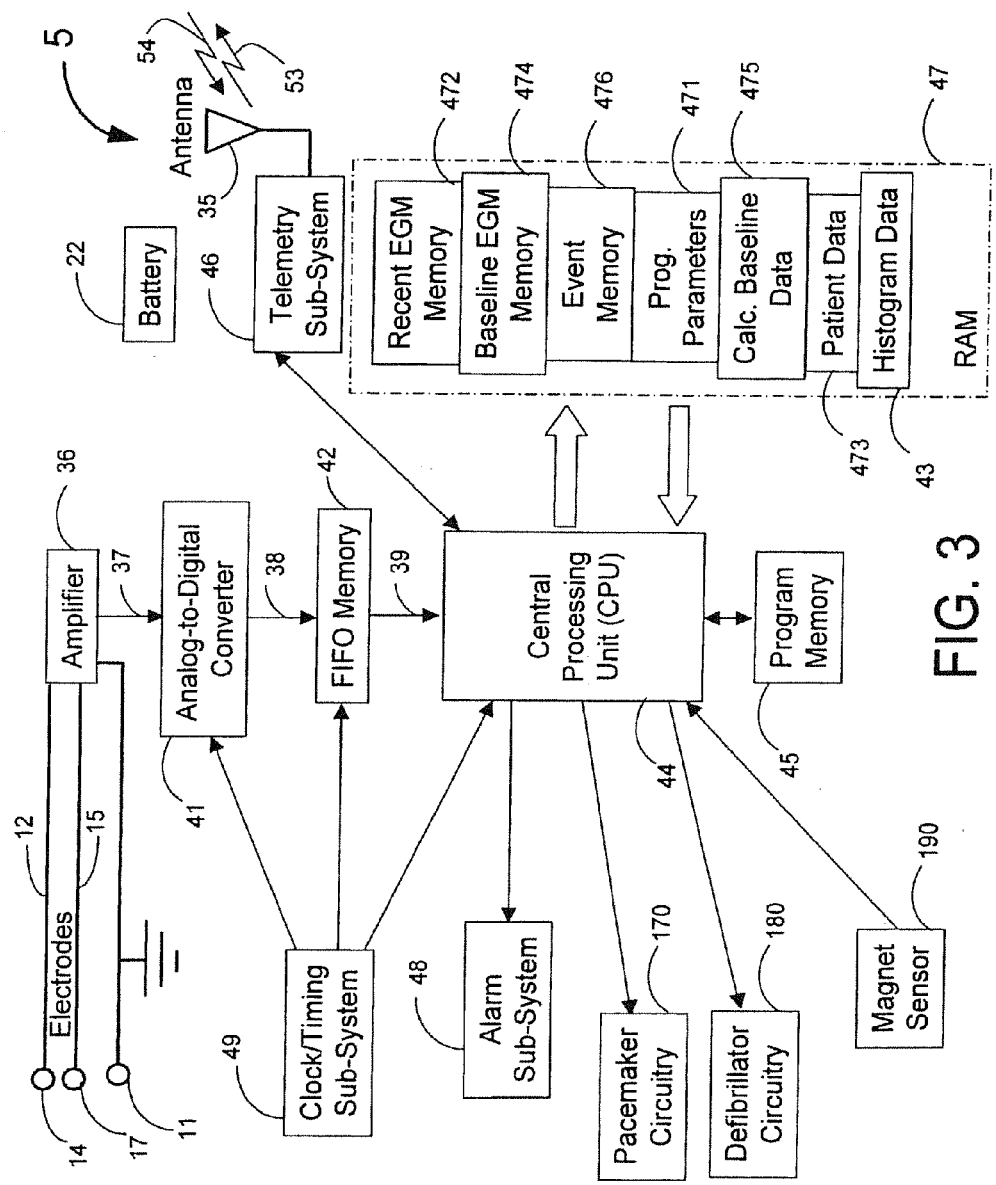
FIG. 3 is a block diagram of the cardiotracker.

FIG. 3 is a block diagram of the cardiotracker 5 with battery 22. The electrodes 14 and 17 connect with wires within the leads 12 and 15 respectively to the amplifier 36 that is also connected to the case 11 acting as an indifferent electrode. As two or more electrodes 14 and 17 are shown here, the amplifier 36 would be a multi-channel amplifier. If only one electrode was used, the amplifier would be a single channel amplifier. The amplified electrogram signals 37 from the amplifier 36 are converted to digital signals 38 by the analog-to-digital converter 41. The digital electrogram signals 38 are buffered in the First-In-First-Out (FIFO) memory 42. A processor shown as the central processing unit (CPU) 44 coupled to memory means shown as the Random Access Memory (RAM) 47 can process the digital electrogram data 38 stored within the FIFO 42 according to the programming instructions stored in the program memory 45. This programming (i.e., software) enables the cardiotracker 5 to detect the occurrence of cardiac events such as an acute myocardial infarction.

A clock/timing sub-system 49 provides the means for timing specific activities of the cardiotracker 5 including the absolute or relative time stamping of detected cardiac events. The clock/timing sub-system 49 can also facilitate power savings by causing components of the cardiotracker 5 to go into a low power standby mode in between times of electrogram signal collection and processing. Such cycled power savings techniques are often used in implantable pacemakers and defibrillators. In an alternative embodiment, the function of the clock/timing sub-system 49 can be provided by a program subroutine run by the central processing unit 44.

In a preferred embodiment of the present invention, the RAM 47 includes specific memory locations for 3 sets of electrogram segment storage. These are the recent electrogram storage 472 that would store the last 2 minutes to 24 hours of recorded electrogram segments so that the electrogram data for the last day (even if there are no events) or in the period just before the onset of a cardiac event can be reviewed at a later time by the patient's physician using the physician's programmer 68 of FIG. 1. For example, the recent electrogram memory 472 might contain eight, 10 second long electrogram segments that were captured every 30 seconds over the prior 4 minute time period. The baseline electrogram memory 474 would also provide storage for baseline electrogram segments collected at preset times over one or more days. For example, the baseline electrogram memory 474 might contain 24 baseline electrogram segments of 10 seconds duration, one from each hour for the prior 24 hours.

The event memory 476 occupies the largest part of the RAM 47. The event memory 476 is not overwritten on a regular schedule as are the current electrogram memory 472 and baseline electrogram memory 474 but is typically maintained until read out by the patient's physician with the programmer 68 of FIG. 1. When a cardiac event such as excessive ST shift indicating an acute myocardial infarction is detected by the CPU 44, all (or part) of the entire contents of the baseline and recent electrogram memories 472 and 474 would typically be copied into the event memory 476 so as to save the pre-event data for later physician review. Following the occurrence of a cardiac event, post event electrogram data would be saved in the event memory 476 for a preset time period.

The RAM 47 also contains memory sections for programmable parameters 471 and calculated baseline data 475. The programmable parameters 471 include the upper and lower limits for the normal and elevated heart rate ranges and physician programmed parameters related to the cardiac event detection processes stored in the program memory 45. The calculated baseline data 475 contain detection parameters extracted from the baseline electrogram segments stored in the baseline electrogram memory 474. Calculated baseline data 475 and programmable parameters 471 would typically be saved to the event memory 476 following the detection of a cardiac event. The RAM 47 also includes patient data 473 that may include the patient's name, address, telephone number, medical history, insurance information, doctor's name, and specific prescriptions for different treatments or medications to be administered by medical practitioners in the event of different cardiac events.

Figure 5:
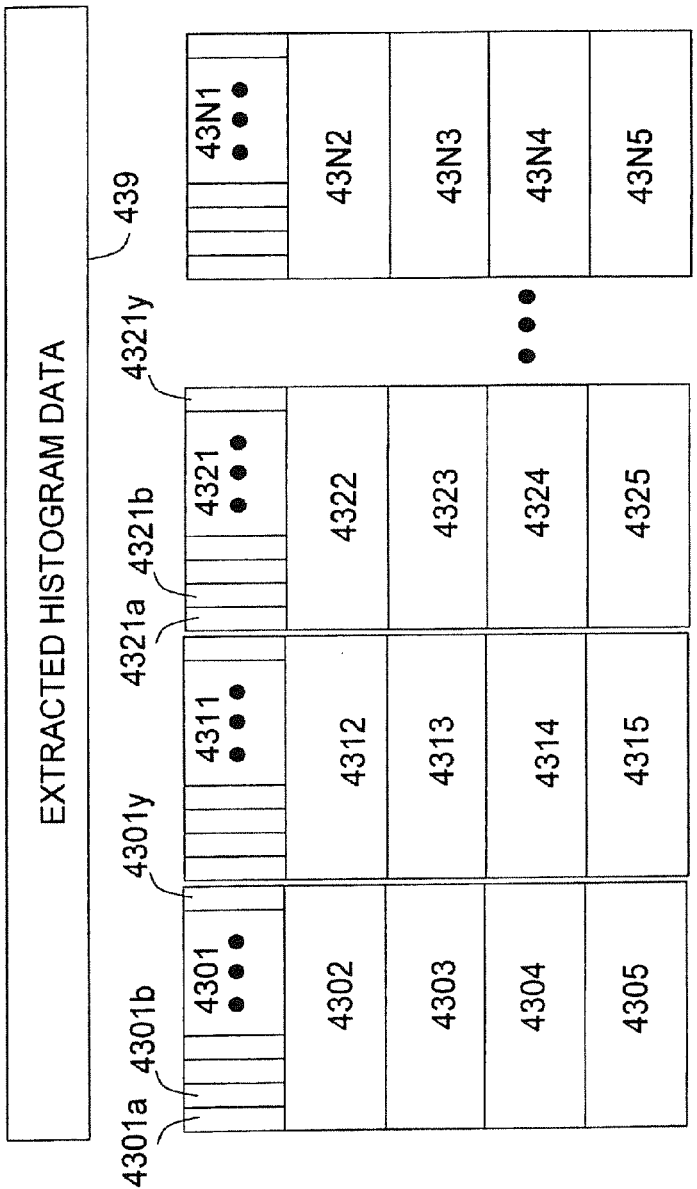
FIG. 5 is a block diagram showing the structure of the histogram data memory.

Finally, the RAM 47 contains histogram data memory 43 whose structure is shown in FIG. 5.

It is envisioned that the cardiotracker 5 could also contain pacemaker circuitry 170 and/or defibrillator circuitry 180 similar to the cardiosaver device described by Fischell et al in U.S. Pat. No. 6,240,049.

The alarm sub-system 48 is the internal alarm means that contains the circuitry and transducers to produce the internal alarm signals for the cardiotracker 5. The internal alarm signal can be a mechanical vibration, a sound or a subcutaneous electrical tickle.

The telemetry sub-system 46 with antenna 35 provides the cardiotracker 5 the means for two-way wireless communication to and from the external equipment 7 of FIG. 1. The outgoing signal 53 being from the cardiotracker 5 to the external equipment 7 and the incoming signal 54 being from the external equipment 7 to the cardiotracker 5. Existing radiofrequency transceiver chip sets such as the CHIPCOM CC1000 or the Ash transceiver hybrids produced by RF Microdevices, Inc. can readily provide such two-way wireless communication over a distance of up to 10 meters from the patient. It is also envisioned that short range telemetry (less than 6 inches) such as that typically used in pacemakers and defibrillators could also be applied to the cardiotracker 5. It is also envisioned that standard wireless protocols such as Bluetooth and 802.11a, 802.11b or 802.11g might be used to allow communication with a wider group of externally located peripheral devices.

A magnet sensor 190 could be incorporated into the cardiotracker 5. An important use of the magnet sensor 190 is to turn on the cardiotracker 5 on just before programming and implantation into a human subject. This would reduce wasted battery life in the period between the times that the cardiotracker 5 is packaged at the factory until the time that it is implanted into the human subject.

Figure 4:
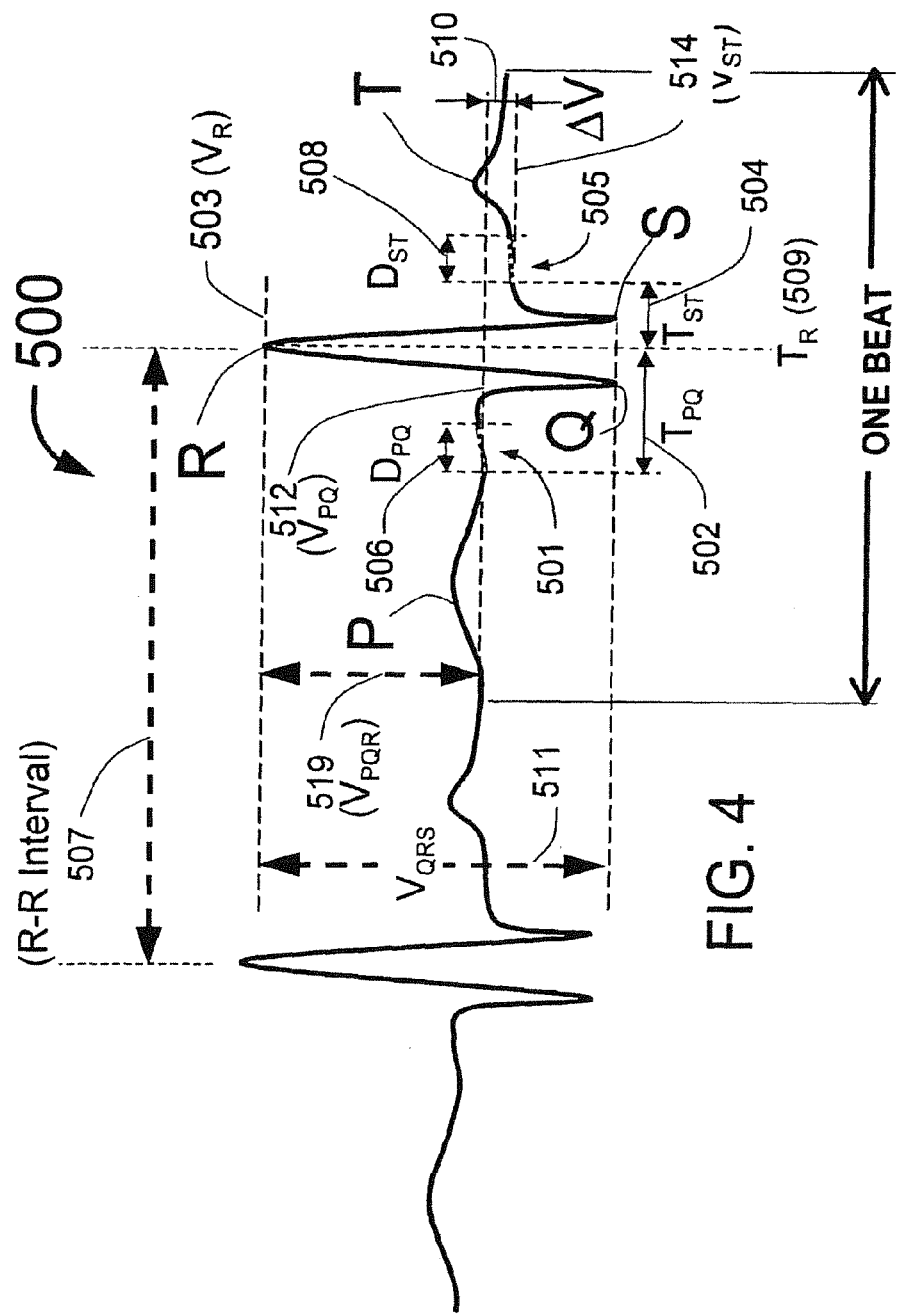
FIG. 4 illustrates a normal electrogram pattern with a set of typical heart signal parameters.

FIG. 4 highlights the features of one normal beat 500 of an electrogram segment and also shows some portions of the prior beat. The beat 500 shows typical heart beat wave elements labeled P, Q, R, S and T. The beat 500 is defined to be a sub-segment of an electrogram segment containing exactly one R wave and including the P and Q elements before the R wave and the S and T elements following the R wave. The R-R interval 507 for the beat 500 is defined as the time from the R wave before the beat 500 to the R wave of the beat 500. Both the prior R wave and the R wave of the beat 500 are shown in FIG. 4.

For the purposes of detection algorithms, different sub-segments, elements and calculated values related to the beat 500 are hereby specified. The peak of the R wave of the beat 500 occurs at the time $T_R$ (509). The PQ segment 501 and ST segment 505 are sub-segments of the normal beat 500 and are located in time with respect to the time $T_R$ (509) as follows:

a. The PQ segment 501 has a time duration $D_{PQ}$ (506) and starts $T_{PQ}$ (502) milliseconds before the time $T_R$ (509).

b. The ST segment 505 has a time duration $D_{ST}$ (508) and starts $T_{ST}$ (502) milliseconds after the time $T_R$ (509).

The ST segment 505 and the PQ segment 501 are examples of sub-segments of the electrogram signal from a patient's heart. The R wave and T wave are also sub-segments. The dashed lines $V_{PQ}$ (512) and $V_{ST}$ (514) illustrate the average voltage amplitudes of the PQ and ST segments 501 and 505 respectively for the normal beat 500. The "ST deviation" $\Delta V$ (510) of the normal beat 500 is defined as:

$$\Delta V(510) = V_{ST}(514) - V_{PQ}(512)$$

The parameters $T_{PQ}$, $T_{ST}$, $D_{PQ}$ and $D_{ST}$ would typically be set with the programmer 68 of FIG. 1 by the patient's doctor at the time the cardiotracker 5 is implanted so as to best match the morphology of the patient's electrogram signal at a normal (e.g., resting) heart rate.

The R height $V_{PQR}$ (519) for the beat 500 is defined as $$V_{PQR}(519) = V_R(503) - V_{PQ}(512)$$

$V_{PQ}$ (512), $V_{ST}$ (514), $V_R$ (503), $V_{PQR}$ (519) and $\Delta V$ (510) are examples of per-beat heart signal parameters for the beat 500.

Although it may be effective to fix the values of start times $T_{PQ}$ (502) and $T_{ST}$ (504) and the time durations $D_{PQ}$ (506) and $D_{ST}$ (508), it is envisioned that the start times $T_{PQ}$ and $T_{ST}$ and the durations $D_{PQ}$ and $D_{ST}$ could be automatically adjusted by the cardiotracker 5 to account for changes in the R-R interval 507 (i.e., changes in the patient's heart rate). If the R-R interval 507 increases or decreases, as compared with the R-R interval for patient's normal heart rate, it is envisioned that the start times $T_{PQ}$ (502) and $T_{ST}$ (504) and/or the durations $D_{PQ}$ (506) and $D_{ST}$ (508) could be adjusted depending upon the R-R interval 507 for a specific beat or the average R-R interval for an entire electrogram segment. A simple technique for doing this would vary the start times $T_{PQ}$ and $T_{ST}$ and the durations $D_{PQ}$ and $D_{ST}$ in proportion to the change in R-R interval. For example, if the patient's normal heart rate is 60 beats per minute, the R-R interval is 1 second. At 80 beats per minute the R-R interval is 0.75 seconds, a 25% decrease. This could automatically produce a 25% decrease in the values of $T_{PQ}$, $T_{ST}$, $D_{PQ}$ and $D_{ST}$. Alternately, the values for $T_{PQ}$, $T_{ST}$, $D_{PQ}$ and $D_{ST}$ could be fixed for each of up to 20 preset heart rate ranges. In either case, it is envisioned that after the device has been implanted, the patient's physician would, through the programmer 68 of FIG. 1, download from the cardiotracker 5 to the programmer 68, a recent electrogram segment from the recent electrogram memory 472 (of FIG. 3). The physician would then use the programmer 68 to select the values of $T_{PQ}$, $T_{ST}$, $D_{PQ}$ and $D_{ST}$ for the heart rate in the downloaded recent electrogram segment. The programmer 68 would then allow the physician to choose to either manually specify the values of $T_{PQ}$, $T_{ST}$, $D_{PQ}$ and $D_{ST}$ for each heart rate range or have the cardiotracker 5 automatically adjust the values of $T_{PQ}$, $T_{ST}$, $D_{PQ}$ and $D_{ST}$ based on the R-R interval 507 for each beat of any electrogram segment collected in the future by the cardiotracker 5. It is also envisioned that only the start times, $T_{PQ}$ and $T_{ST}$, might be automatically adjusted and the time durations $D_{PQ}$ and $D_{ST}$ would be fixed so that the average values of the ST and PQ segments $V_{PQ}$ (512), $V_{ST}$ (514), $V'_{PQ}$ (512') and $V'_{ST}$ (514') would always use the same number of data samples for averaging.

While the simplest method of adjusting the start times $T_{PQ}$ and $T_{ST}$ is to adjust them in proportion to the R-R interval 507 from the preceding R wave to the R wave of the current beat, a preferred embodiment of the present invention is to adjust the start times $T_{PQ}$ and $T_{ST}$ in proportion to the square root of the R-R interval 507 from the preceding R wave to the R wave of the current beat. It is also envisioned that a combination of linear and square root techniques could be used where $T_{ST}$ and $D_{ST}$ could be set to be proportional to the square root of the R-R interval while $T_{PQ}$ and $D_{PQ}$ could be linearly proportional to the R-R interval.

When pacemaker circuitry 170 is used with the cardiotracker 5, it envisioned that the start time $T_{ST}$ and duration $D_{ST}$ of the ST segment may have different values depending on whether or not the heart is being paced. When the pacemaker is pacing the heart, the ST segment shifts so as to occur later relative to the start of the R wave as compared to the position of the ST segment when the pacer is not pacing the heart. It is also envisioned, that the offset for the start of the ST segment may be better measured from the S wave instead of the R when the pacemaker is not pacing. The technique of using different timing parameters for start and duration when pacing can be applied to analysis of any sub-segment of the electrogram including the sub-segment that includes the T wave peak. When the pacemaker circuitry 170 is used with the cardiotracker 5, the algorithm for measurement of the ST segment can be adjusted to respond to either the pacing or no-pacing condition of the pacemaker circuitry 170.

An example of a sequence of steps used to calculate the ST deviation 510 for the normal beat 500 is as follows:

1. Identify the time $T_R$ (509) for the peak of the R wave for the beat 500,

2. Calculate the R-R interval 507 and use that value to look up in a table or calculate the values of the start times $T_{PQ}$, $T_{ST}$ and the time durations $D_{PQ}$ and $D_{ST}$, 3. Average the amplitude of the PQ segment 501 between the times ($T_R - T_{PQ}$) and ($T_R - T_{PQ} + D_{PQ}$) to create the PQ segment average amplitude $V_{PQ}$ (512), 4. Average the amplitude of the ST segment 505 between the times ($T_R + T_{ST}$) and ($T_R + T_{ST} + D_{ST}$) to create the ST segment average amplitude $V_{ST}$ (514), and 5. Subtract $V_{PQ}$ (512) from $V_{ST}$ (514) to produce the ST deviation, $\Delta V$ (510) for the beat 500.

At preset time intervals during the day the cardiotracker 5 will calculate the "average baseline ST deviation" $\Delta V_{BASE}$ defined as the average of the ST deviations $\Delta V$ (510) for at least two beats of a baseline electrogram segment. Typically the ST deviation of 4 to 8 beats of the baseline electrogram segment will be averaged to produce the average baseline ST deviation $\Delta V_{BASE}$ which can be used for later comparison with the ST deviation of recent beats to identify changes indicative of a cardiac event such as an acute myocardial infarction. Fischell et al in U.S. Pat. No. 6,609,023 describe in detail the methods for detecting AMI and exercise induced ischemia.

As (for example) the ST deviation, $\Delta V$ (510) or the QRS voltage, $V_{QRS}$ (511) for each beat is calculated, one or more histograms stored in the histogram data memory 43 of FIGS. 3 and 5 will be incremented with that specific value of that heart signal parameter.

FIG. 5 is an example of a structure for the histogram data memory 43 of the cardiotracker 5 of FIG. 3. The histogram data memory 43 contains two types of histogram data, raw histogram data stored in the memory sections 430 through 43N and extracted histogram data stored in the extracted histogram data memory 439. One of the raw histogram data sections 430 through 43N will always be the section currently being incremented as individual beats are processed by the processor 44 of FIG. 3 to compute the value of one or more heart signal parameters for each processed beat. The other histogram sections will usually be the histograms collected during prior data collection time periods.

In this example, each section 430 through 43N has 5 histograms (e.g., section 430 has histograms 4301, 4302, 4303, 4304 and 4305). Each of the 5 histograms in each section has a multiplicity of bins (e.g., histogram 4301 has bins 4301a, 4301b through 4301y). Each bin is a counter that is typically stored in one to 3 bytes of the histogram data memory 43.

As the cardiotracker 5 processes a beat of the patient's electrogram, one or more heart signal parameters will be measured or computed for the beat. For each processed beat, the counter value of one bin in one of the histograms of the current histogram section will be incremented by one.

The choice of which bin in which histogram is incremented will be based on two heart signal parameters. The selection of one of the 5 histograms will be based on the value of a first heart signal parameter and the choice of which bin is to be incremented will depend upon the value of a second heart signal parameter. Specifically, a specific histogram will be selected if the value of the first heart signal parameter is within the range of the first heart signal parameter associated with that specific histogram. Similarly, a bin within the selected histogram will be incremented if the value of the second heart signal parameter is within the range of the second heart signal parameter associated with that bin.

Figure 6A:
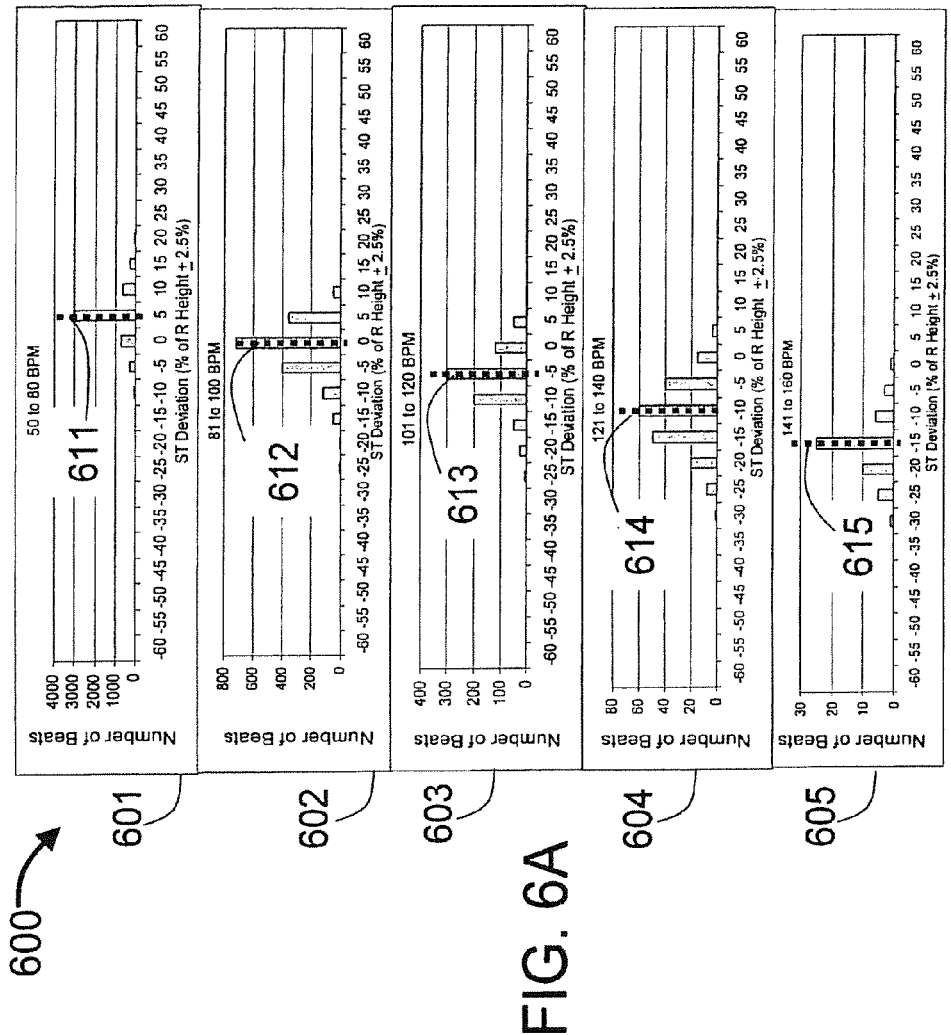
FIG. 6A is an example of a programmer display screen showing a set of histograms for ST deviation for a single data collection time period (viz., one day), where each histogram corresponds to a different heart rate range.

For example, if the data collection time period used for tracking a heart signal parameter, like ST deviation, is one day and collected data retention time period is one week, then N=7 (i.e., section 43N is section 437) and there will be 8 sections 430 through 437 in the histogram memory 43 with seven sections storing the data for each one of seven prior days and the eighth section storing the data for the current day. In this example, each of the five histograms per section correspond to a different range of R-R interval (or heart rate) [the first heart signal parameter] and each bin within a histogram corresponds to a different range of ST deviation [the second heart signal parameter]. As a further example, section 4301 corresponds to heart rates that are between 50 and 80 bpm and each of the bins 4301a through 4301y would correspond to a 5% wide (.+−.2.5%) range of ST deviation as a percentage of baseline R height. Furthermore bin 4103a would correspond to a range of ST deviation of −60%.+−.2.5% of baseline R height and bin 4301y would correspond to a range of ST deviation of +60%.+−.2.5% of baseline R height. Therefore the bin 4301n (not shown) would correspond to a range of ST deviation between +2.5% and +7.5% (i.e., 5%.+−.2.5) of the average baseline level of ST deviation. This bin 4301n would have the data shown as the highest bar of graph 601 in FIG. 6A. In FIG. 6A it is shown that there are a total of 25 bins in each of the histograms 601-605 inclusive. These bins run from −60% plus or minus 2.5% to +60% plus or minus 2.5%. The 14.sup.th bin is 4301n which is +5% plus or minus 2.5% and the 25.sup.th bin in section 4301 is 4301y which is +60% plus or minus 2.5%. The five different heart rate ranges shown for the histograms 601 to 605 inclusive of FIG. 6A would (for example) correspond to the sections 4301 to 4305 inclusive of FIG. 5.

It is envisioned that the levels of ST deviation can be representative of actual voltages (e.g., millivolts) or they may be a normalized value with respect to the signal amplitude of the beat or electrogram segment. Examples of such a signal amplitude is the QRS voltage $V_{QRS}$ (511) or the R wave height above the PQ segment which is $V_{PQR}$ (519) of FIG. 4.

In FIG. 5, if section 432 is the present day's current histogram, then section 431 is from the day before, section 430 from 2 days before, and because the data rolls over, 437 (not shown) is the histogram for 3 days before, 436 (not shown) from 4 days before, 435 (not shown) from 5 days before, 434 (not shown) from 6 days before and section 433 (not shown) from 7 days before. For each beat analyzed by the cardiotracker for the current day's histogram, the R-R interval (heart rate) for that beat is used to select one of the histograms 4321 through 4325 and the value of ST deviation computed for that beat will be used to select the bin in the selected histogram that will be incremented by 1. Further using the labeling of FIG. 4, assume the R-R interval for the beat just analyzed is within the heart rate range of the first histogram 4321 of the current section 432 and the ST deviation 510 of the beat analyzed is −0.1 millivolts which is −1% of the R height 519. In this case the bin corresponding to a range of ST deviations that includes −1% of R height will be incremented by 1. In this way each beat is counted in one bin of one histogram of the current section, in this case, section 432. Over a 24 hour period as the patient's heart rate (R-R interval) goes up and down, the histograms will track the ST deviation of each beat processed in each of the ranges of heart rate.

At the end of the data collection time period (24 hours in this example) during which section 432 is the current section, the cardiotracker will clear section 433 (the section with the oldest data) of all previously stored data and make section 433 (now empty) the current section for data collection. The previous current section 432 now becomes the section from one day before and is saved until the cycle repeats. On the day following the day where section 437 is the current day, section 430 will become the current section.

It is envisioned that before clearing section 433, the cardiotracker might extract or analyze the data in 433 and save the extracted data in the extracted histogram data memory 439. For example, the median value of ST deviation could be calculated for section 432 and that data could be time stamped as to the day of the year and placed into the extracted histogram data memory 439. Alternately, the extracted data placed in the extracted histogram data memory 439 may be calculated for the current histogram section 432 at the end of the data collection time period where the section 432 was designated as the current section.

Examples of extracted data for any data collection time period can include any one, some or all of the following:

1. number of beats in a histogram exceeding an ST deviation or ST shift threshold,
2. average ST deviation or average ST shift,
3. standard deviation of ST deviation or ST shift distribution (may include both positive and negative standard deviation values),
4. total number of beats in the histogram (if there are very few beats in a particular histogram, using the average and/or standard deviation could be misleading),
5. ST deviation or ST shift bin with greatest number of beats,
6. the moving average over 2 or more data collection time periods of any of items 1 through 5 immediately above,
7. the average of the QRS or RS width, and
8. the average QRS voltage.

When the patient's physician downloads the data from the histogram data memory 43 (of FIG. 3), the histograms for the current data collection time period up to the time of download, and the complete histograms for the previous collected data retention time period can all be viewed using the physician's programmer 68 of FIG. 1.

Although the examples above used one day per section as the data collection time period, shorter or longer periods are envisioned. Although 8 sections, (representing 7 days plus a current day's histogram section) are described above, with sufficient memory, a month (32 sections), a year (367 sections) or more of data can be saved in this format.

Although 5 histograms per section are described in the example above, it is envisioned that as few as one and as many as 100 could be used to collect relevant data. There are a number of heart signal parameters including QRS width or RS width of the electrogram wave form and R-R interval variability indicative of changes in the balance of the patient's sympathetic and parasympathetic nervous systems that are most likely to be tracked in a single histogram per data collection time period. Other heart signal parameters such as ST deviation, ST segment voltage, ST shift (ST deviation relative to average baseline ST deviation), T wave height, QRS voltage and/or R wave height may be preferably tracked with respect to heart rate (determined from R-R interval) using multiple histograms per section.

It is envisioned, that the data collection time period could be as short as a minute and as long as many months. A preferred embodiment uses a data collection time period of one day as collection on a daily basis would eliminate any affects from daily cycles (i.e., from circadian rhythm). A data collection time period of less than an hour would be useful to collect ST deviation vs. heart rate data during a stress test in the doctor's office. The data collected during such a stress test could be compared to earlier tests using analysis tools built into the physician's programmer 68 of the tracker system 10. Histogram data does not require large amounts of data storage. For example, each of the five histograms 4321 through 4325 of FIG. 5 might have 25 bins 4321*a*, 4321*b* through 4321*y*, with each bin requiring 2 bytes of data storage. Thus only 50 bytes are needed per histogram and 250 bytes for the entire section 432. The eight sections would therefore require only 2 kilobytes, approximately 7.5 kilobytes would suffice for a month's (30 days) data and approximately 90 kilobytes for a year of data. Being able to store a one week to twelve month history of cardiovascular condition within the cardiotracker would be of tremendous value to cardiologists in diagnosing the progression of cardiovascular disease. Two byte bins are typically sufficient for a day's data as the cardiotracker is designed to only monitor some fraction of the beats (e.g., 10 seconds out of every 30 seconds) and a two byte counter could handle every third beat for 54 hours. If a longer data collection time period than 4 days is required, three bytes could handle more than year's worth of data where a third of all beats are captured. Four bytes per bin would be sufficient to count every heart beat for one hundred years.

It is also envisioned that the physician's programmer 68 of FIG. 1 could include the capability to manually clear the data in the current histogram. This would allow a "clean slate" for data collection from a stress test where, as each beat is analyzed, the ST deviation data build up is a representation of the patient's cardiovascular condition. It is also envisioned that a special cardiotracker data collection mode where every beat is analyzed could be enabled to collect more data during such a stress test. If every beat is too high a burden on the cardiotracker processor, then the cardiotracker might process a higher percentage of beats than during standard cardiotracker operation.

The actual turnover time for automated clearing of the oldest histograms at the end of each data collection time period would be programmable (e.g., midnight of the patient's time zone for a one day data collection time period). If the manual clearing function is used, it is envisioned that the current section of histogram memory would still be used until the next turnover time.

FIG. 6A is an example of a histogram set 600 consisting of five histograms 601 through 605 inclusive representing an example of a programmer display screen of a single section of histogram data memory 43 of FIG. 3 for a single data collection time period (viz., one day). In FIG. 6A, the horizontal scale is the ST deviation (i.e., ST segment voltage minus PQ segment voltage) as a percent of the R height, V.sub.PQR (519) of FIG. 4. Also in FIG. 6A, the vertical scale of each histogram 601 through 605 is the number of beats in the data collection time period (viz., one day) where the ST deviation was in one of the ranges listed on the horizontal scale of the histogram. Each of the five histograms 601 through 605 represents all the beats processed (during the data collection time period of one day) that had R-R intervals corresponding to the heart rate range for that histogram. It is envisioned that the heart rate (or R-R interval) ranges for each histogram 601 through 605 may be either permanently set or programmable using the physician's programmer 68 of FIG. 1. In the histograms 601 through 605 each bin represents a range of ST deviation expressed as a percentage of the R height, V.sub.PQR (519) as shown in FIG. 4. Each bin represents the shown value of −60, −55, −50, . . . +60, in percent of R height plus or minus 2.5%. Therefore, each bin covers a range (i.e., a class interval) of 5% of the R height 519. The bin showing the value 5 (i.e., +5%) in histogram 601 would be incremented by one every time a beat with an R-R interval corresponding to a heart rate of 50 to 80 bpm had an ST deviation between 2.5% and <7.5% of the R height of that beat. The next higher bin would be 7.5% to <12.5% of the R height, and so on. It is also envisioned that instead of using the R height 519 of each beat as the reference, the average R height of a multiplicity of beats of a baseline electrogram segment would be used as a reference.

Although the heart rate range for histogram 602 in FIG. 6A is shown as 81 to 100 bpm, the cardiotracker will classify any beat whose R-R interval corresponds to a heart rate greater than 80 bpm and less than or equal to 100 bpm as belonging in this heart rate range. Similarly the heart rate range labels of 101 to 120 bpm (histogram 603), 121 to 140 bpm (histogram 604) and 141 to 160 bpm (histogram 605) will include beats with R-R intervals corresponding to heart rates of >100 to <120 bpm, >120 to <140 bpm and >140 to <160 bpm. This correspondence is also applied to the charts in FIGS. 6B, 7A, 7B, 8A and 8B wherever heart rate ranges are specified.

The technique of expressing ST deviation as a percentage of R height 519 compensates for signal level variations from causes such as long term changes in electrode impedance or changes in the gain of an amplifier. As an alternative, it is also envisioned that the actual voltage or signal level or the percentage of a preset maximum signal level for the ST deviation (e.g., millivolts) could be used as the range for each bin in the histograms 601 through 605. For example, the bins in 601 might represent between −60% to +60% of a maximum signal level of 10 millivolts. Thus the bin labeled 5 would be incremented if the ST deviation was between 2.5% and 7.5% of 10 millivolts (i.e., 0.25 to 0.75 millivolts). The technique described here will work with preset bin ranges. Preferably, this invention envisions bin ranges that can be set by the physician using the physician's programmer 68 of FIG. 1.

Also shown in FIG. 6A are the median (or average) values 611 through 615 inclusive of the histograms 601 through 605 respectively. The median value and number of beats counted in a histogram are useful extracted data that would typically be saved in the extracted histogram data memory 439 of FIG. 5. The medians and numbers of beats can also be used to compute moving averages by either the cardiotracker 5 or programmer 68 of FIG. 1. It is envisioned that comparison of the medians and/or the moving averages to pre-set thresholds can be used to alert the patient to a significant change in their cardiovascular condition.

Figure 6B:
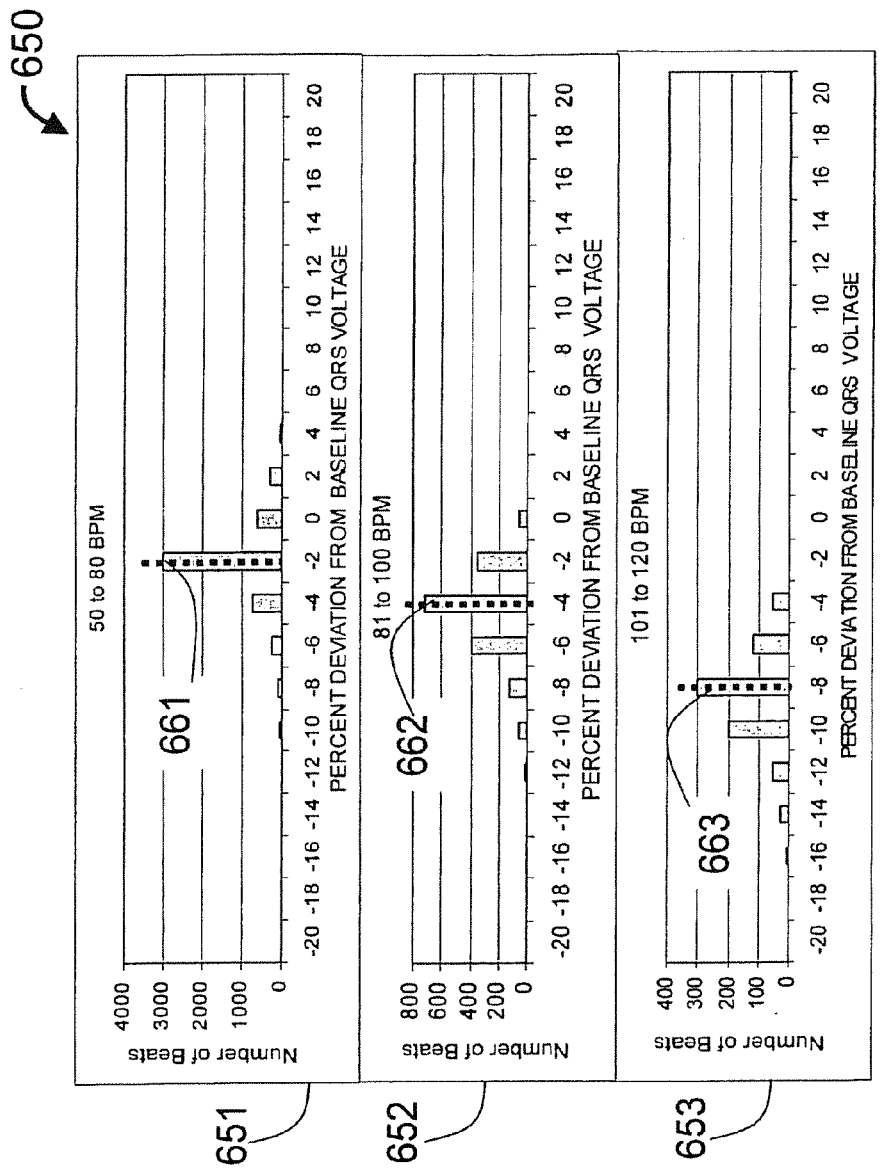
FIG. 6B is an example of a programmer display screen showing a set of histograms for the percent deviation of the QRS voltage from a baseline QRS voltage for a single data collection time period (viz., one day), where each histogram corresponds to a different heart rate range.

FIG. 6B shows a set of histograms 650 consisting of the histograms 651, 652 and 653 at three different ranges of heart rate (50 to 80, 81 to 100 and 101 to 120 bpm) for the heart signal parameter QRS voltage calculated as a percent deviation from the baseline QRS voltage. In FIG. 6B, the horizontal scale represents 41 histogram bins (from −20% to +20%) with each bin corresponding to the labeled percent deviation of QRS voltage from the baseline QRS voltage plus or minus 1%. Also in FIG. 6B, the vertical scale represents the number of heart beats whose percentage deviation from the baseline QRS voltage fell within each of the 41 bins during the data collection time period (e.g., one day). For example, for the histogram 651, in the bin labeled "−2" there were 3,000 recorded beats that had a percentage difference between the measured QRS voltage and the baseline QRS voltage between −3% and −1%. For example, if the baseline QRS voltage was 10 millivolts, histogram 651 shows that there were 3,000 beats with measured QRS voltage between 9.7 and 9.9 millivolts. Similarly, the bin to the right of the −2% bin of histogram 651 indicates that approximately 600 beats during the data collection time period had a QRS voltage within .+−0.1% of the baseline QRS voltage.

The dashed lines 661, 662 and 663 represent the average values −2%, −4% and −8% of the histograms 651, 652 and 653 respectively. The average value dashed lines 661, 662 and 663 represent respectively the median (or mean) values of the percent QRS voltage deviation for three different heart rate ranges, namely: 50-80 bpm, >80-100 bpm and >100 to 120 bpm for the histograms 651, 652 and 653. The heart rate ranges can be set and adjusted by the medical practitioner using the programmer 68 of FIG. 1.

Figure 7A:
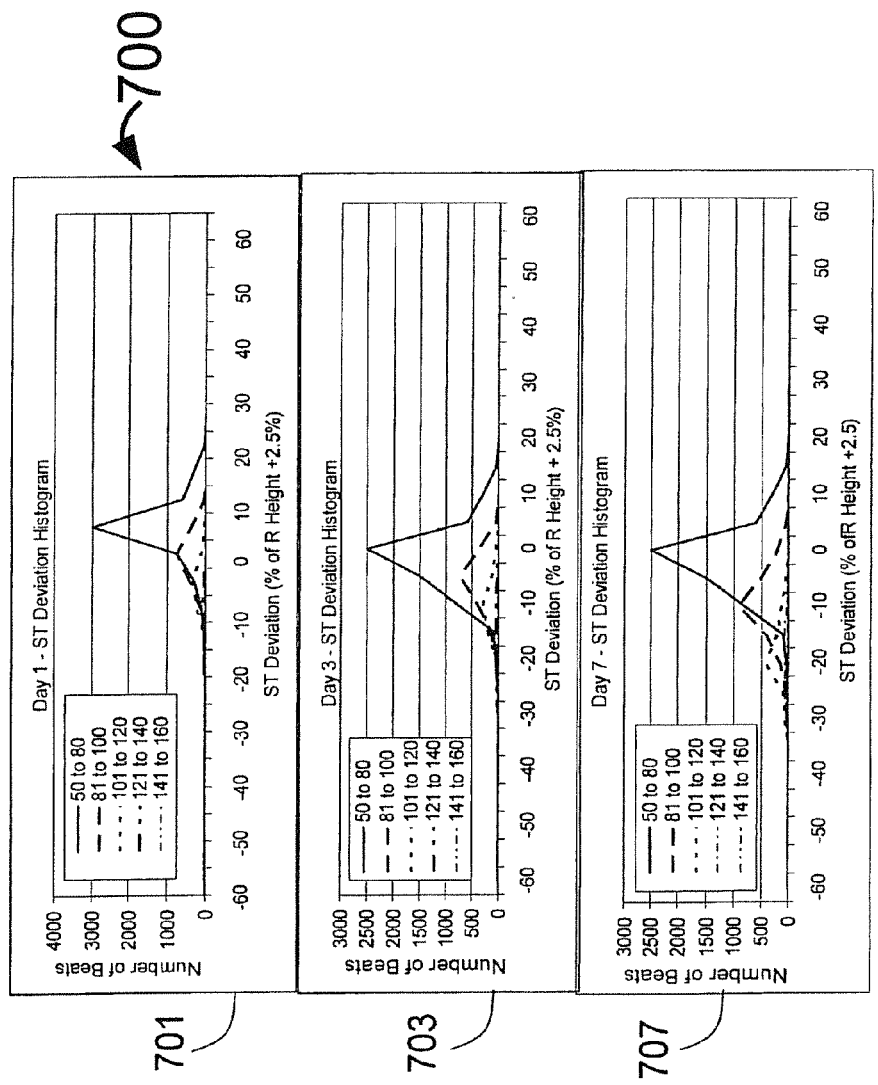
FIG. 7A is an example of a programmer display screen showing ST deviation histograms for three different days, where each frequency plot shows 5 different heart rate ranges on one graph with multiple lines.
Figure 8A:
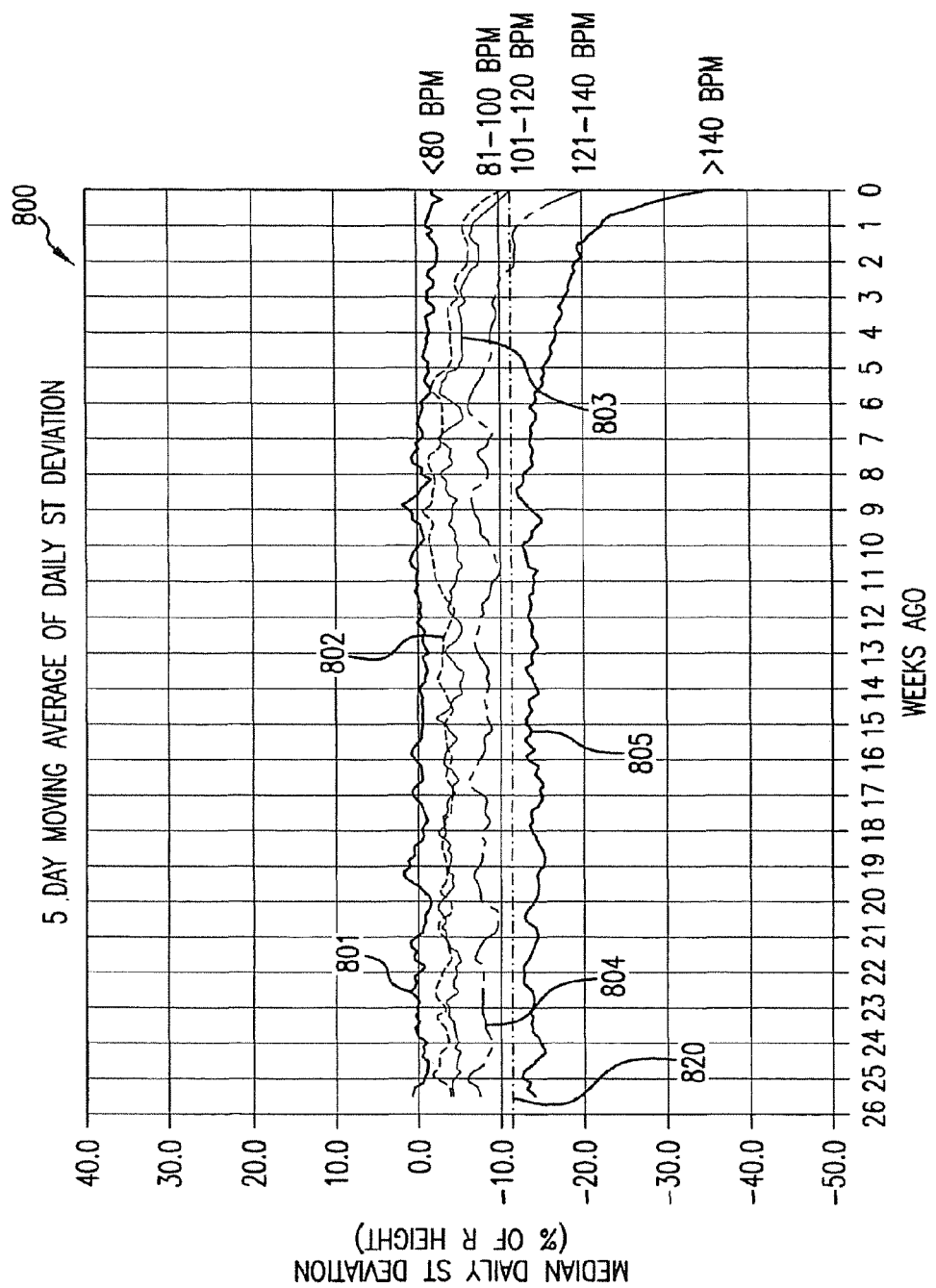
FIG. 8A is an example of the programmer display screen showing a graphical representation of the 5 day moving average of the daily average ST deviation for each of five heart rate ranges over a period of 26 weeks.

FIG. 7A is a histogram display 700 that shows five different heat rate ranges of histograms for three different days 701, 703 and 707. This representation would typically be shown as a screen on the physician's programmer 68 of FIG. 1. The display 700 of FIG. 7A would allow the physician to examine trends in the ST deviation vs. heart rate over time. This example clearly shows in day 7 (chart 707) that there is a significant change in the distribution of ST deviation at higher heart rates as compared with days 1 and 3. This would be indicative of a narrowing or partial occlusion of one or more coronary arteries in the heart. Although this is a good way to look at changes between two different time periods, the display of FIG. 8A is a preferred means to clearly see such changes. It is also envisioned that instead of the distributions of ST deviation as shown in FIG. 7A, the average or median ST deviations for each heart rate range could be displayed as a single vertical bar or line.

Figure 7B:
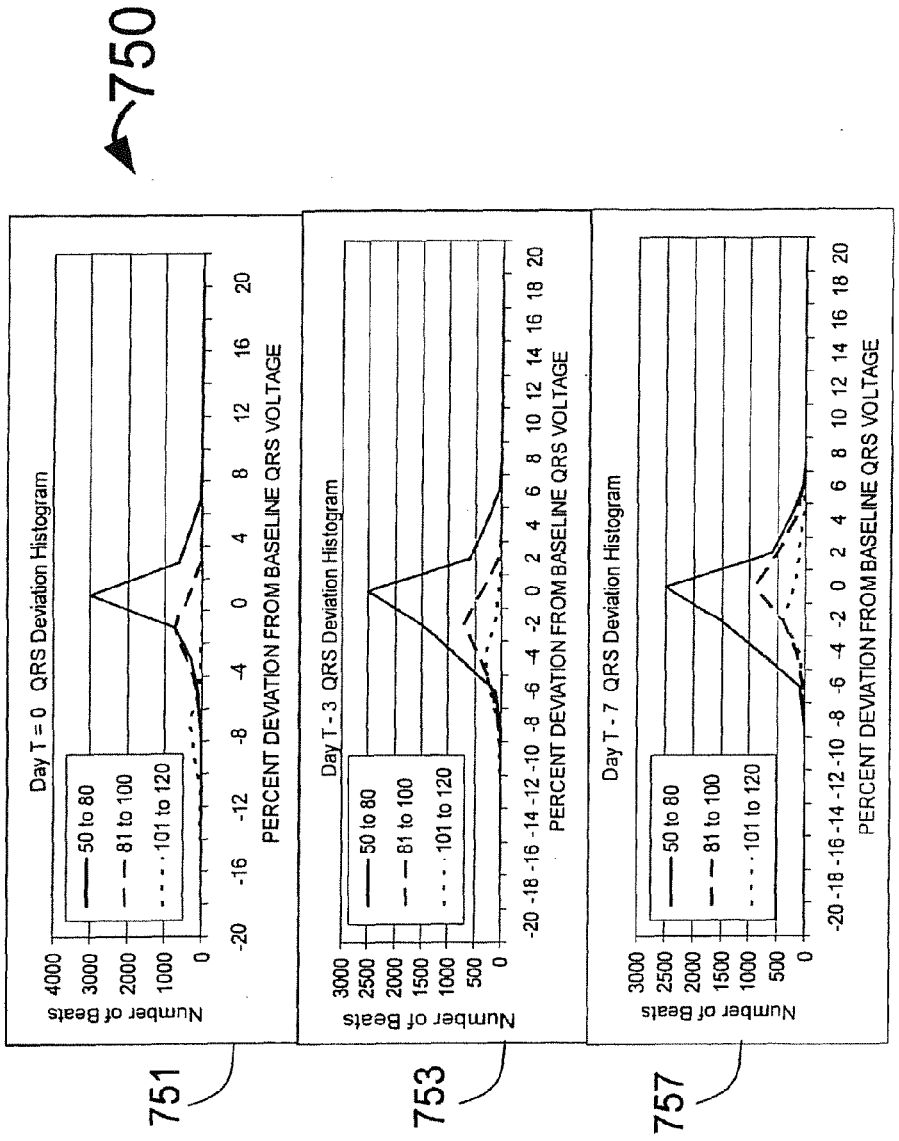
FIG. 7B is an example of a programmer display screen showing histograms for the percent deviation of the QRS voltage from the baseline QRS voltage for three specific days and for three different ranges of heart rate.

FIG. 7B is a histogram display 750 that shows three different heart rate ranges for three different days 751, 753 and 757. Comparable to FIG. 7A, FIG. 7B shows the histograms for QRS voltage for a multiplicity of beats plotted as a percent deviation from the baseline QRS voltage.

FIG. 8A is a graphical representation 800 of the five day moving average of the average daily ST deviation for each of five heart rate ranges 801 through 805 inclusive for a period of 26 weeks (6 months). The display 800 as shown in FIG. 8A, would be of tremendous value to a cardiologist in recognizing a gradual but potentially life threatening change in a patient's cardiovascular condition. As a patient with the cardiotracker 5 of FIG. 1 goes about daily activities their heart rate will go up and down. Each beat analyzed by the cardiotracker (typically between 6 and 80 beats in any particular minute) will increment the appropriate heart rate range related histogram allowing the cardiotracker 5 to store the daily distributions of ST deviation in the five different heart rates. While the cardiotracker 5 may only store the histogram data for a week or two, the extracted histogram data memory 439 of FIG. 5 could be used to store extracted histogram data for a much longer period of time. In fact, the use of extracted histogram data is an extremely efficient way to track the changes in heart signal parameters over an extended period of time. For example storing the average ST deviation and number of beats in each of five daily histograms (5 heart rate ranges) requires only 15 bytes per day within the extracted histogram data memory 439. This translates to approximately 450 bytes per month and 5,500 bytes per year. This efficient data storage can be compared with electrogram data storage where at 200 samples per second, 30 seconds of electrogram storage requires 6,000 bytes of data storage.

The display 800 could result from calculations made by the programmer 68 of FIG. 1 after downloading six months worth of daily histograms or extracted histogram data from the cardiotracker 5. Alternatively, the programmer 68 could combine data downloaded from the cardiotracker 5 on multiple occasions. Moving averages could also be calculated within the cardiotracker 5 or within the programmer 68 from the daily average or median value for ST deviation using the beat count extracted from the histogram data. Such calculations would not overly tax the power consumption on the cardiotracker 5 as the calculations would require at most a few seconds of processor time per day.

It is also envisioned that the cardiologist might set an alarm threshold 820 for any or all heart rate range curves so that when one or more of the five day moving averages of ST deviation crosses the limit, the patient would be alerted. Different thresholds for each heart rate range could also be implemented. In the example of FIG. 8A, the alarm threshold 820 for the 121-140 bpm heart rate range 804 was set to −12% of the R height, and a SEE DOCTOR ALERT would have been initiated by the cardiotracker 5 two weeks before the current date. It is envisioned that the programmer 68 would allow the physician to set these detection thresholds. The programmer 68 would also allow the physician to specify what type of alarm will be generated by the cardiotracker 5 if the detection threshold is passed, e.g., either a SEE DOCTOR ALERT or an EMERGENCY ALARM. It is also envisioned that detection thresholds could be set for the slope of the curves of FIG. 8A so that significant downward slope of ST deviation would initiate a patient alert. Also, it is envisioned that a combination of a specific value above the threshold 820 when combined with a specific downward slope could also be used to trigger a SEE DOCTOR ALERT.

Instead of using the fixed threshold 820 for triggering a SEE DOCTOR ALERT from the 5 day moving average of the average ST deviation for each heart rate range, an adaptive threshold that is based on the difference between the maximum and minimum of the 5 day moving average curves exceeding a preset threshold is a preferred embodiment for the present invention.

The processing of extracted histogram data would typically be performed once per day although longer and shorter data collection time periods are also envisioned. An example of the extraction process for average ST deviation would be as follows:

1. Once per data collection time period (e.g., once per day), the ST deviation histogram data collected during the previous data collection time period is summarized, stored and analyzed. For each heart rate range, estimates are made of the average (e.g., mean and/or median) ST deviation, the average −1 sigma and the average +1 sigma of the ST deviation.

2. Other data, e.g., number of analyzed beats in each heart rate range and the average 24 hour baseline signal amplitude (e.g., R height or QRS voltage) may also be stored as part of the summary data.

3. An N day moving average (N is typically between 1 and 30) of the daily average (e.g., mean or median) ST deviation for each heart rate range is then determined, along with the maximum and minimum values of the N day moving averages for each heart rate range.

If the difference between the maximum moving average and the minimum moving average of the ST deviation for any of the ST deviation moving average curves 801 through 805 exceeds a preset threshold, an ST deviation histogram trending event for that heart rate range can be detected. If enabled, a SEE DOCTOR ALERT would then be triggered.

The hour at which the daily extraction would occur is programmable by the doctor so that detection of such a trending event would trigger the SEE DOCTOR ALERT at time that is convenient to the patient (e.g., not while he would be sleeping). Once a SEE DOCTOR ALERT has been triggered and the patient has had therapy (e.g., a stent or angioplasty procedure) that relieves the ST depression (or elevation) the programmer 68 of FIG. 1 can be used to reset the start date for future histogram trending analysis so that the ST shift data that caused the alert in the past is not used in future analysis. An alternative technique to accomplish this is to clear all previously stored histogram data from the cardiotracker memory once the ST shift has been treated. Therefore any new analysis would not include the data that caused the histogram trending event. The prior data would however, remain in the programmer 68 for later review and tracking of the patient's history.

For example, once per day at noon, to avoid alerting the patient when he might be asleep, the cardiotracker could calculate the daily average (mean or median) ST deviation from the histogram for each heart rate range (e.g., 601 through 605) of FIG. 6A. The cardiotracker would then calculate the 5 day moving average that includes the just calculated daily average ST deviation and the averages from the four previous days. The cardiotracker could then identify the maximum and minimum values of the moving average data for each heart rate range after a start date set by the programmer 68. If the difference between the maximum and minimum values exceeds a preset threshold for any heart rate range, then a histogram trending event is detected and, if enabled, a SEE DOCTOR ALERT would be triggered in the implanted cardiotracker 5.

Figure 8B:
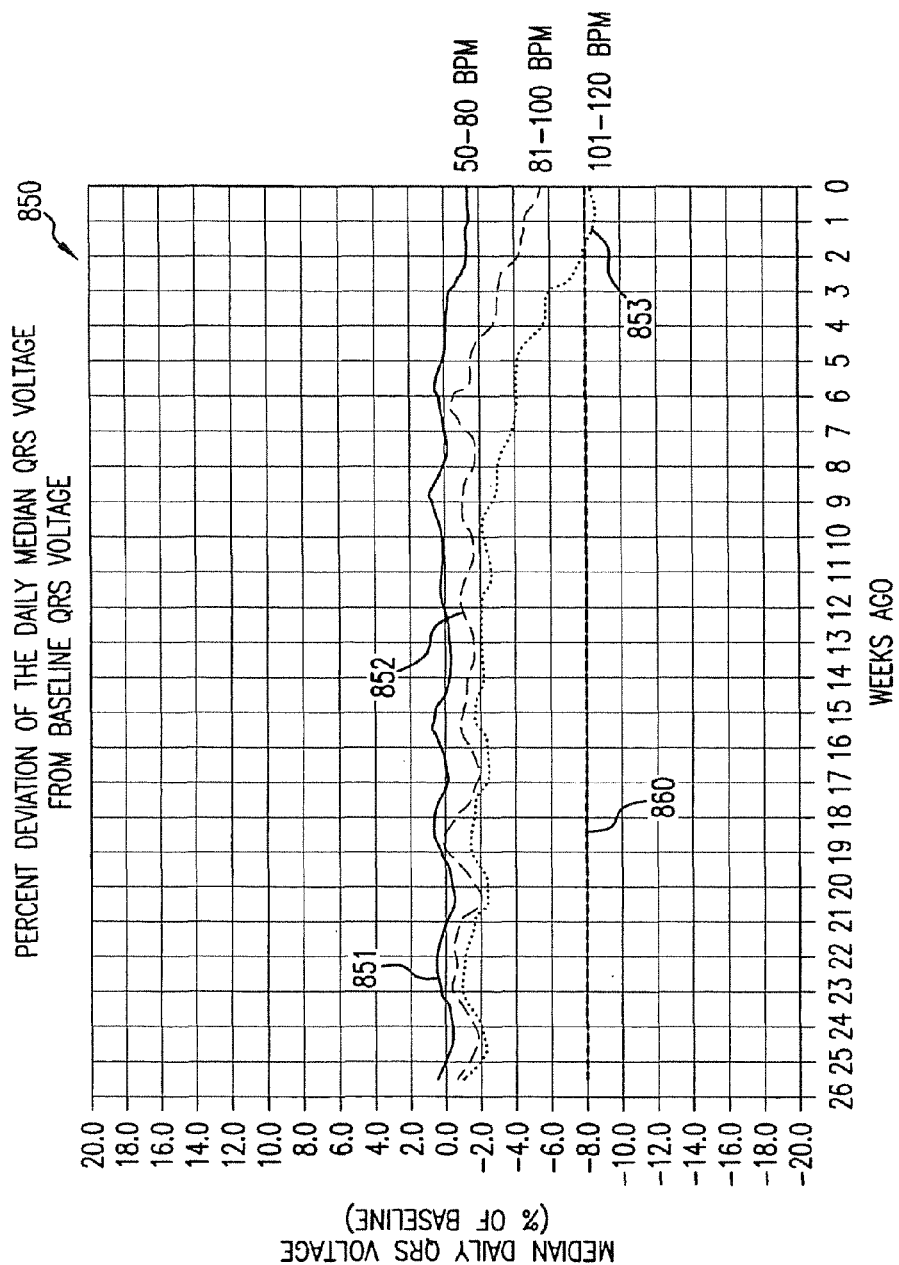
FIG. 8B is an example of the programmer display screen showing a graphical representation of the percent deviation of the daily median QRS voltage from the baseline QRS voltage for each of three heart rate ranges over a period of 26 weeks.

FIG. 8B illustrates a display 850 on the physician's programmer 68 for the median (or mean) value of the percent deviation of QRS voltage over a six month period compared to a baseline QRS voltage. The display 850 shows the percent deviation for QRS voltage for three different heart rate ranges corresponding to the heart rate ranges shown for FIGS. 6B and 7B. The three curves, 851, 852 and 853 correspond respectively to the heart rate ranges of 50-80 bpm, 81-100 bpm and 101 to 120 bpm.

It is expected that the display 850 of FIG. 8B would be of great value to doctors who treat heart transplant patients. Specifically, it has been shown by Warnecke, et al that a decrease of 8% in the QRS voltage from a baseline QRS voltage value from a time when the heart is not being rejected can indicate rejection of a transplanted heart at an early enough time to change the patient's medication to save that heart. The present "gold standard" for detecting rejection is a biopsy that (starting two years after implant) is typically carried out only once each six month time period. This biopsy is done in a catheterization laboratory and it is typically difficult for the patient and quite expensive. Also, if rejection occurs starting at some time between the six month biopsy procedures, then that early detection of rejection will not be possible. If however, a patient has an implanted cardiotracker 5 that has an alarm that is triggered by the −8% decrease in QRS voltage, then that SEE DOCTOR ALERT setting 860 as shown in FIG. 8B will occur and the heart in that transplant patient can be saved by appropriate medication therapies. It is envisioned that the setting of the level 860 for triggering a SEE DOCTOR ALERT could be between −1% and −20% below the baseline value of the QRS voltage. Furthermore, one could combine a negative slope of any of the curves of FIG. 8B with a higher value for triggering the SEE DOCTOR ALERT. For example, if a slow descent of the percent deviation of QRS voltage utilized a −8% drop as the level to set off the SEE DOCTOR ALERT, it is envisioned that a level of (let us say) −6% could be used to set off the SEE DOCTOR ALERT if the downward slope corresponded to (let us say) a −1% per week decrease in QRS voltage. Thus the patient would be warned two weeks earlier that he is going to reach the level of −8% when his doctor would prescribe a change in the patient's medication regime.

While it may be sufficient to detect transplant rejection when the deviation of average daily QRS voltage as compared to the baseline QRS voltage exceeds a preset threshold for a single day, it may be more reliable to require that the threshold be exceeded for two or more consecutive days. An example of the extraction process for average (mean or median) QRS voltage would be as follows:

1. Once per data collection time period (e.g., once per day), the QRS voltage data collected during the previous data collection time period is summarized, stored and analyzed. For each heart rate range, calculations are made of the average (e.g., mean and/or median) QRS voltage and the average −1 sigma and average +1 sigma deviations of the QRS voltage.

2. Other data, e.g., number of analyzed beats in each heart rate range baseline R height for the past 24 hours could also be stored as part of the summary data.

If the average QRS voltage has declined more than a preset percentage of the baseline QRS voltage, a transplant rejection event for that heart rate range will be detected. If enabled, a SEE DOCTOR ALERT would then be triggered. The baseline QRS voltage is an average QRS voltage captured at an earlier time when the transplanted heart was not experiencing rejection. It is also envisioned that to reduce the possibility of a false positive detection, a SEE DOCTOR ALERT would only be triggered after a specified number of successive transplant rejection events. For example, it might require two or three successive transplant rejection events to trigger the alert.

The hour at which the daily extraction of collected data would occur is programmable by the doctor so that detection of such an event would trigger the SEE DOCTOR ALERT at a time that is convenient to the patient (e.g., not while the patient would be sleeping). Once a SEE DOCTOR ALERT has been triggered and the patient has had therapy (e.g., an increase in cyclosporine) that reverses the rejection episode, the programmer 68 of FIG. 1 can be used to reset the baseline QRS voltage so that the data that caused the alert is in the past and is not used in future analysis.

For example, once per day at noon, the cardiotracker will calculate the daily average (mean or median) QRS voltage from the histogram for each heart rate range (e.g., the heart rate ranges 651 through 653 of FIG. 6B). If the difference between the recently calculated average QRS voltage and the baseline QRS voltage exceeds a preset threshold 860 for any heart rate range, then a transplant rejection event is detected and if enabled, a SEE DOCTOR ALERT (or possibly an EMERGENCY ALARM) is triggered.

Although a decline in the average QRS voltage is cited here as a known means for early detection of rejection for a transplanted heart, it is also envisioned that some other heart signal parameter may be equally or better suited for that purpose. Specifically, ST deviation or ST shift, R wave slope, QRS complex width or another heart signal parameter could be used for the early detection of rejection of a transplanted heart. Furthermore, it is envisioned to place an accelerometer onto the end of an epicardial or endocardial lead, which end is firmly attached to the heart muscle, to detect a change in heart wall motion that could be indicative of early rejection. The combination of a means to measure heart wall motion with a second means to detect a change in a heart signal parameter is also envisioned as a means for early detection of the rejection of a transplanted heart.

Although ST deviation and QRS voltage have been the primary examples used here for histogram data collected based on a patient's heart rate, it is envisioned that any other heart signal parameter measured or calculated can be usefully used with this histogram methodology. Examples of such parameters include QRS or RS complex width, ST shift (ST deviation compared to a baseline ST deviation), R wave width, T wave shape, T wave alternans, changes in R-R interval variability and number of overly long R-R intervals. These parameters may be monitored independent of the patient's heart rate, or separate histograms could be used for each of multiple heart rate ranges.

Although the present invention has described the use of histogram memory for cardiovascular electrical signals, these techniques are also applicable for electrical signals collected using electrodes from other portions of the human body. Such electrical signals include signals from the human brain, gastrointestinal tract, the liver, the pancreas and musculature. Any of these organs may (for example) have a change in their electrical signal that might indicate an early stage of rejection. Furthermore, although only electrogram related histograms have been described herein, it should be understood that other measurements including measurements by heart motion sensors, temperatures at certain places in the body and devices to measure pressure and/or $pO_2$ may be used to generate histograms of cardiovascular condition of the patient.

It is also envisioned that all of the processing techniques described herein for an implantable cardiotracker are applicable to a tracker system configuration using skin surface electrodes and a non-implanted cardiotracker. For systems that were totally external to the patient, the term "electrogram" would be replaced by the term "electrocardiogram". Thus the cardiotracker device described in FIGS. 1 through 3 inclusive would also function as a monitoring device that is completely external to the patient.

It is important to note that many of the functions of the tracker system as described herein that are programmable by a medical practitioner could be preset in manufacture to typical settings that are useful for most patients. Thus the doctor could use this default mode instead of trying to set particular alarm parameters for a particular patient. Furthermore, the physician's programmer 68 could have a default mode to restore all the settings of either or both the cardiotracker 5 and external alarm system 60 to values that are recommended by the manufacturer. There may also be separate default settings for men and woman and others that would be related to a specific medical problem that the patient has.

Although the histogram technique is a preferred embodiment of the present invention as it greatly reduces the amount of memory needed to store the values of a heart signal parameter for each beat analyzed during a data collection time period, it is also envisioned that the each measured or calculated value of one or more heart signal parameters could be directly stored in memory. For example, the value of ST deviation would be measured for each beat during a one hour data collection time period (e.g., during a stress test). These values would all be stored in memory and at the end of the data collection time period, the average ST deviation for each heart rate range could be calculated from the stored values. This technique would be of greatest value where the data collection time period is shorter than a day.

Various other modifications, adaptations, and alternative designs are of course possible in light of the above teachings. Therefore, it should be understood at this time that, within the scope of the appended claims, the invention can be practiced otherwise than as specifically described herein.

What is claimed is:

1. A method for tracking the cardiovascular condition of a human patient, including the steps of:
    (a) sensing an electrical signal from the patient's heart, the electrical signal comprising a multiplicity of beats;
    (b) computing from the electrical signal a heart signal parameter value associated with at least one of the multiplicity of beats;
    (c) computing a heart rate value based on the at least one of the multiplicity of beats;
    (d) selecting one of a plurality of histograms stored in a histogram memory to update according to the heart rate value, wherein each histogram includes a plurality of histogram bins;
    (e) during a data collection time period, incrementing one of the plurality of histogram bins, wherein the selection of the histogram bin to be incremented is dependent on the computed value of the heart signal parameter;
    (f) after the end of the data collection time period, calculating a statistical value of the heart signal parameter from the selected histogram;
    (g) storing the statistical value in memory; and
    (h) calculating a detection threshold for abnormal values of the heart signal parameter based on the statistical value.

2. The method of claim 1 wherein the statistical value is the mean value of the heart signal parameter.

3. The method of claim 1 wherein the statistical value is the median value of the heart signal parameter.

4. The method of claim 1 further including the step of calculating the standard deviation of the value of the heart signal parameter value, and wherein the detection threshold is based on the mean plus the standard deviation.

5. The method of claim 1 wherein the data collection time period is 24 hours.

6. The method of claim 1 wherein the histogram memory is within an implantable device.

7. The method of claim 6 further including the step of transmitting histogram data from the implantable device to an external programmer, and wherein the detection threshold is calculated by a programmer.

8. The method of claim 1 further including the step of counting the number of beats characterized by values of the heart signal parameter that exceed the detection threshold.

9. The method of claim 1 selection of the histogram bin to be incremented is dependent on only the computed value of the heart signal parameter for a single beat.

* * * * *